US012496442B2

(12) United States Patent
Chao et al.

(10) Patent No.: US 12,496,442 B2
(45) Date of Patent: Dec. 16, 2025

(54) MICRONEEDLE ELECTROPORATION DEVICE

(71) Applicant: Industrial Technology Research Institute, Hsinchu (TW)

(72) Inventors: Bo-Kai Chao, Taipei (TW); Ying-Hao Wang, Pintung County (TW); Jui-Hung Tsai, Miaoli County (TW); Chih-Hao Hsu, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 1206 days.

(21) Appl. No.: 17/361,507

(22) Filed: Jun. 29, 2021

(65) Prior Publication Data

US 2022/0032049 A1 Feb. 3, 2022

Related U.S. Application Data

(60) Provisional application No. 63/046,060, filed on Jun. 30, 2020.

(51) Int. Cl.

*A61N 1/32* (2006.01)
*A61M 37/00* (2006.01)
*A61N 1/04* (2006.01)

(52) U.S. Cl.

CPC ......... *A61N 1/327* (2013.01); *A61M 37/0015* (2013.01); *A61N 1/0412* (2013.01); (Continued)

(58) Field of Classification Search

CPC . A61N 1/327; A61N 1/0412; A61M 37/0015; A61M 2037/0007; A61M 2037/0023

See application file for complete search history.

(56) References Cited

U.S. PATENT DOCUMENTS 5,439,440 A * 8/1995 Hofmann ............... A61N 1/327 604/20
5,964,726 A * 10/1999 Korenstein ............ C12M 35/02 604/20

(Continued)

FOREIGN PATENT DOCUMENTS

CN 104307098 B 9/2016
CN 108310617 A 7/2018

(Continued)

OTHER PUBLICATIONS

Taiwan Patent Office, Office Action, Patent Application Serial No. 110123771, Nov. 2, 2021, Taiwan.

(Continued)

*Primary Examiner* — Bhisma Mehta
*Assistant Examiner* — Mark A Igel

(57) ABSTRACT

A microneedle electroporation device is provided, including a housing, a positioning member, an intermediate plate, a first microneedle assembly, a second microneedle assembly, a socket, a first wire, and a second wire. The positioning member is connected to the housing and the intermediate plate. The intermediate plate includes a plurality of first holes and a plurality of second holes. The first microneedle assembly includes a plurality of first microneedles and a first metal connecting portion connected to the first microneedles. The first microneedles pass through the first holes. The second microneedle assembly includes a plurality of second microneedles and a second metal connecting portion connected to the second microneedles. The second microneedles pass through the second holes. The first microneedle assembly and the second microneedle assembly are electrically independent of each other. The first wire connects the socket to the first metal connecting portion. The (Continued)

second wire connects the socket to the second metal connecting portion.

20 Claims, 27 Drawing Sheets

(52) U.S. Cl.
CPC ............... *A61M 2037/0007* (2013.01); *A61M 2037/0023* (2013.01)

(56) References Cited

U.S. PATENT DOCUMENTS

| | | | | |
|---|---|---|---|---|
| 9,630,004 | B2 | 4/2017 | Rajguru et al. | |
| 10,010,447 | B2 * | 7/2018 | Kashani | A61F 9/0008 |
| 10,124,159 | B2 * | 11/2018 | Kemmerrer | A61M 37/0015 |
| 11,241,242 | B2 * | 2/2022 | Park | A61B 17/205 |
| 2002/0016562 | A1 * | 2/2002 | Cormier | A61B 5/150099 604/20 |
| 2003/0225360 | A1 * | 12/2003 | Eppstein | A61N 1/044 604/19 |
| 2007/0066959 | A1 * | 3/2007 | Seward | A61M 37/0015 604/20 |
| 2007/0161964 | A1 * | 7/2007 | Yuzhakov | A61M 37/0015 604/272 |
| 2008/0312647 | A1 * | 12/2008 | Knopp | A61B 18/1477 606/41 |
| 2011/0172639 | A1 * | 7/2011 | Moga | A61M 5/14224 604/506 |
| 2019/0240469 | A1 * | 8/2019 | McAllister | A61M 37/0015 |
| 2020/0197679 | A1 * | 6/2020 | Li | B29C 45/2626 |
| 2020/0360072 | A1 * | 11/2020 | Kuang | A61B 18/10 |
| 2022/0023605 | A1 * | 1/2022 | Zvezdin | A61K 9/0021 |
| 2022/0032049 | A1 * | 2/2022 | Chao | A61N 1/327 |

FOREIGN PATENT DOCUMENTS

| | | | | | |
|---|---|---|---|---|---|
| CN | 109394237 | A | * | 3/2019 | A61B 5/150022 |
| CN | 109963604 | A | | 7/2019 | |
| CN | 109966636 | A | | 7/2019 | |
| CN | 113926072 | A | * | 1/2022 | |
| CN | 118217523 | A | * | 6/2024 | |
| DE | 60225859 | T2 | * | 4/2009 | A61B 5/14514 |
| EP | 2409727 | B1 | | 10/2018 | |
| EP | 2327419 | B1 | | 5/2020 | |
| EP | 3021930 | B1 | | 10/2020 | |
| TW | BI626965 | | | 6/2018 | |
| WO | WO-2007035710 | A2 | * | 3/2007 | A61B 17/205 |
| WO | WO-2013187392 | A1 | * | 12/2013 | A61M 37/0015 |

OTHER PUBLICATIONS

Wei, Zewen, et al., "A flexible microneedle array as low-voltage electroporation electrodes for in vivo DNA and siRNA delivery", Lab on a Chip, 2014, pp. 4093-4102, Thw Royal Society of Chemistry, US.

Wilke, N., et al., "Silicon microneedle electrode array with temperature monitoring for electroporation" Sensors and Actuators A, Jul. 2005, 7 pages, Elsevier B. V. US.

Yan, Keshu, et al. "Transdermal drug delivery by in-skin electroporation using a microneedle array" International Journal of Pharmaceutics, 2010, pp. 77-83, Elsevier B. V. US.

* cited by examiner

720

MICRONEEDLE ELECTROPORATION DEVICE

TECHNICAL FIELD

The application relates in general to a microneedle electroporation device, and in particular, to a microneedle electroporation device which can generate an electric field.

BACKGROUND

Vaccines are capable of starting a humoral immune response and then producing antibodies, or activating lymphocytes, such as cytotoxic T cells through a cellular immune response to resist the invasion of a pathogenic organism and prevent occurrence of disease. However, using nucleic acid vaccines as an example, after being injected into the human body by the current injecting method, some types of vaccines cannot be recognized by the human body, and cannot produce an immune response. Therefore, how to address the aforementioned problem has become an important issue.

BRIEF SUMMARY OF INVENTION

To address the deficiencies of conventional products, an embodiment of the invention provides a microneedle electroporation device, including a housing, a positioning member, an intermediate plate, a first microneedle assembly, a second microneedle assembly, a socket, a first wire, and a second wire. The housing has an accommodating space, and the positioning member is connected to the housing. The intermediate plate is connected to the positioning member, and includes a first surface, a second surface, a plurality of first holes, and a plurality of second holes, wherein the first surface faces the accommodating space, and the second surface is opposite to the first surface. The first holes and the second holes penetrate the intermediate plate from the first surface to the second surface. The first microneedle assembly is disposed between the positioning member and the intermediate plate, and includes a plurality of first microneedles and a first metal connecting portion. The first microneedles pass through the first holes, and the first metal connecting portion is connected to the first microneedles. The second microneedle assembly is disposed between the positioning member and the intermediate plate, and includes a plurality of second microneedles and a second metal connecting portion. The second microneedles pass through the second holes, and the second metal connecting portion is connected to the second microneedles. The first microneedle assembly and the second microneedle assembly are electrically independent of each other. The socket is disposed on the housing. The first wire connects the socket to the first metal connecting portion. The second wire connects the socket to the second metal connecting portion.

A microneedle electroporation device is also provided, including a housing, a positioning member, an intermediate module, a first microneedle assembly, a second microneedle assembly, a socket, a first wire, and a second wire. The housing has an accommodating space, and the positioning member is connected to the housing. The intermediate module is connected to the positioning member, and includes a plurality of plates, wherein a plurality of first holes and a plurality of second holes are formed between the plates. The first microneedle assembly includes a plurality of first microneedles. The first microneedles pass through the first holes, and are electrically connected to each other. The second microneedle assembly includes a plurality of second microneedles. The second microneedles pass through the second holes, and are electrically connected to each other. The socket is disposed on the housing. The first microneedle is electrically connected to the socket via the first wire. The second microneedle is electrically connected to the socket via the second wire.

BRIEF DESCRIPTION OF DRAWINGS

The present invention can be more fully understood by reading the subsequent detailed description and examples with references made to the accompanying drawings, wherein.

DETAILED DESCRIPTION OF INVENTION

The making and using of the embodiments of the microneedle electroporation device are discussed in detail below. It should be appreciated, however, that the embodiments provide many applicable inventive concepts that can be embodied in a wide variety of specific contexts. The specific embodiments discussed are merely illustrative of specific ways to make and use the embodiments, and do not limit the scope of the disclosure.

Unless defined otherwise, all technical and scientific terms used herein have the same meaning as commonly understood by one of ordinary skill in the art to which this invention belongs. It should be appreciated that each term, which is defined in a commonly used dictionary, should be interpreted as having a meaning conforming to the relative skills and the background or the context of the present disclosure, and should not be interpreted in an idealized or overly formal manner unless defined otherwise.

Figure 1:
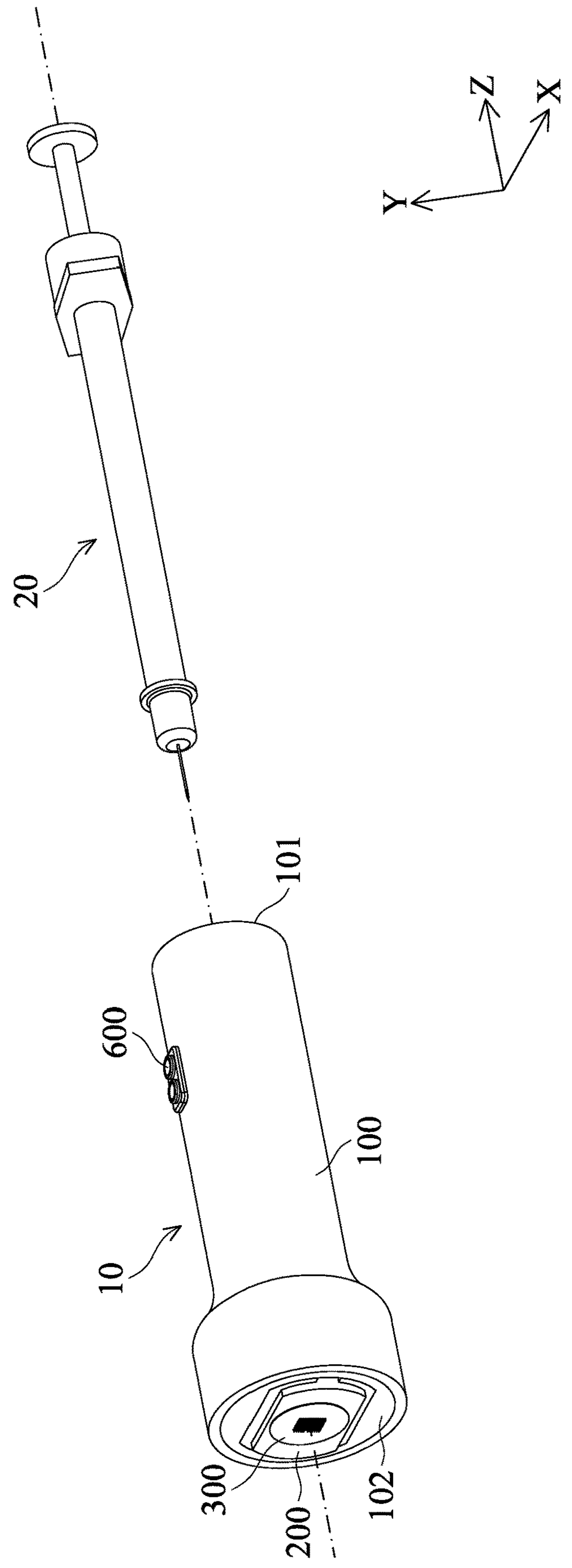
FIG. 1 is a schematic diagram of a microneedle electroporation device and an injecting device according to an embodiment of the invention.

Referring to FIG. 1, a microneedle electroporation device 10 in an embodiment of the invention can be used to connect an injecting device 20 and an external power feeding device (not shown, such as a power supply). When the injecting device 20 injects liquid into the skin of the human, the microneedle electroporation device 10 can create a uniform electric field around the injecting position, so as to generate notch(s) on the cell membranes of the cells around the injecting position. Therefore, the liquid can flow into the cells via the notch(s). For example, if the liquid is a vaccine solution (such as a nucleic acid vaccine solution), it will be help to produce the immune response when the liquid entering the cells.

Figure 2:
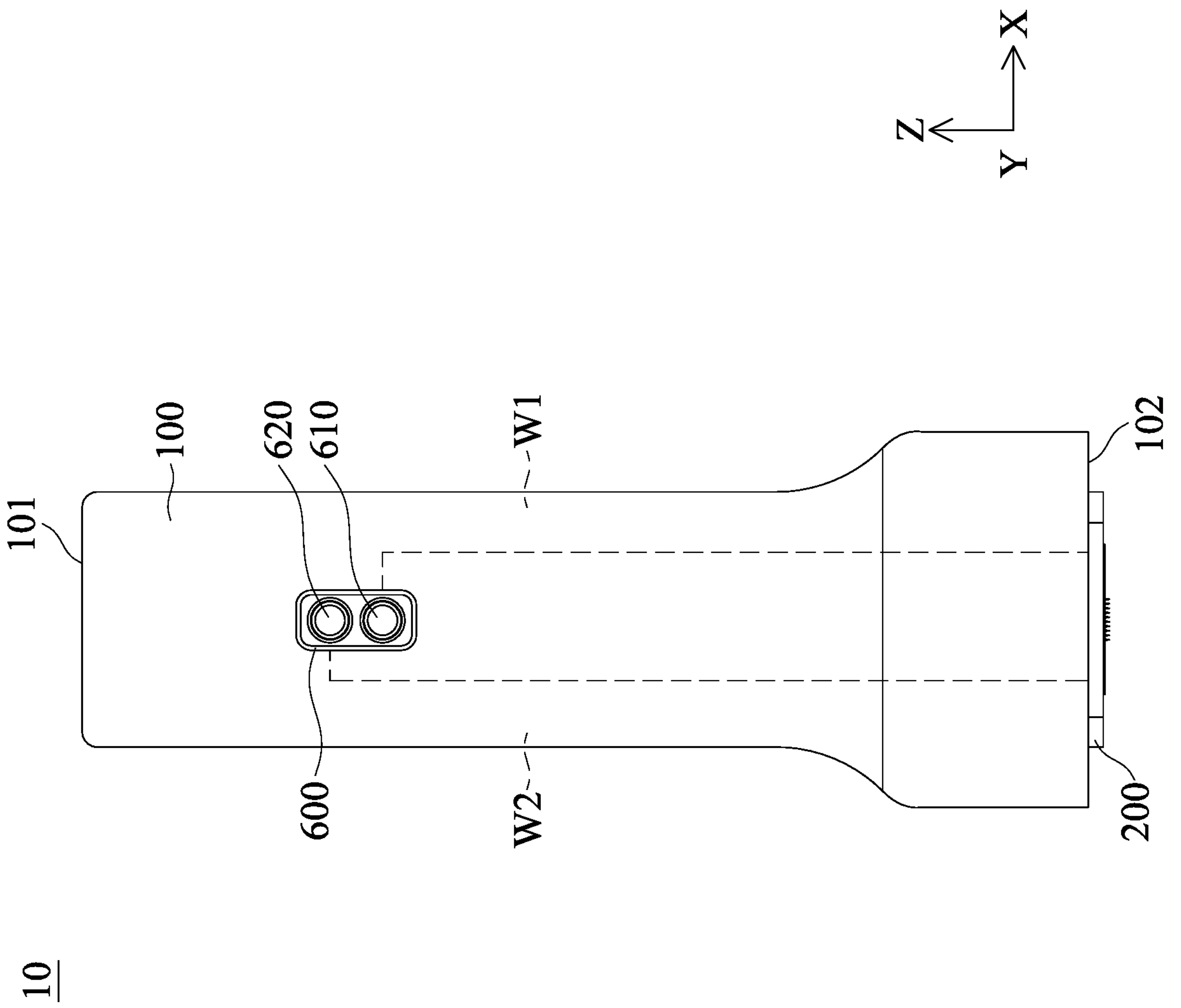
FIG. 2 is a schematic diagram of the microneedle electroporation device according to an embodiment of the invention.
Figure 3:
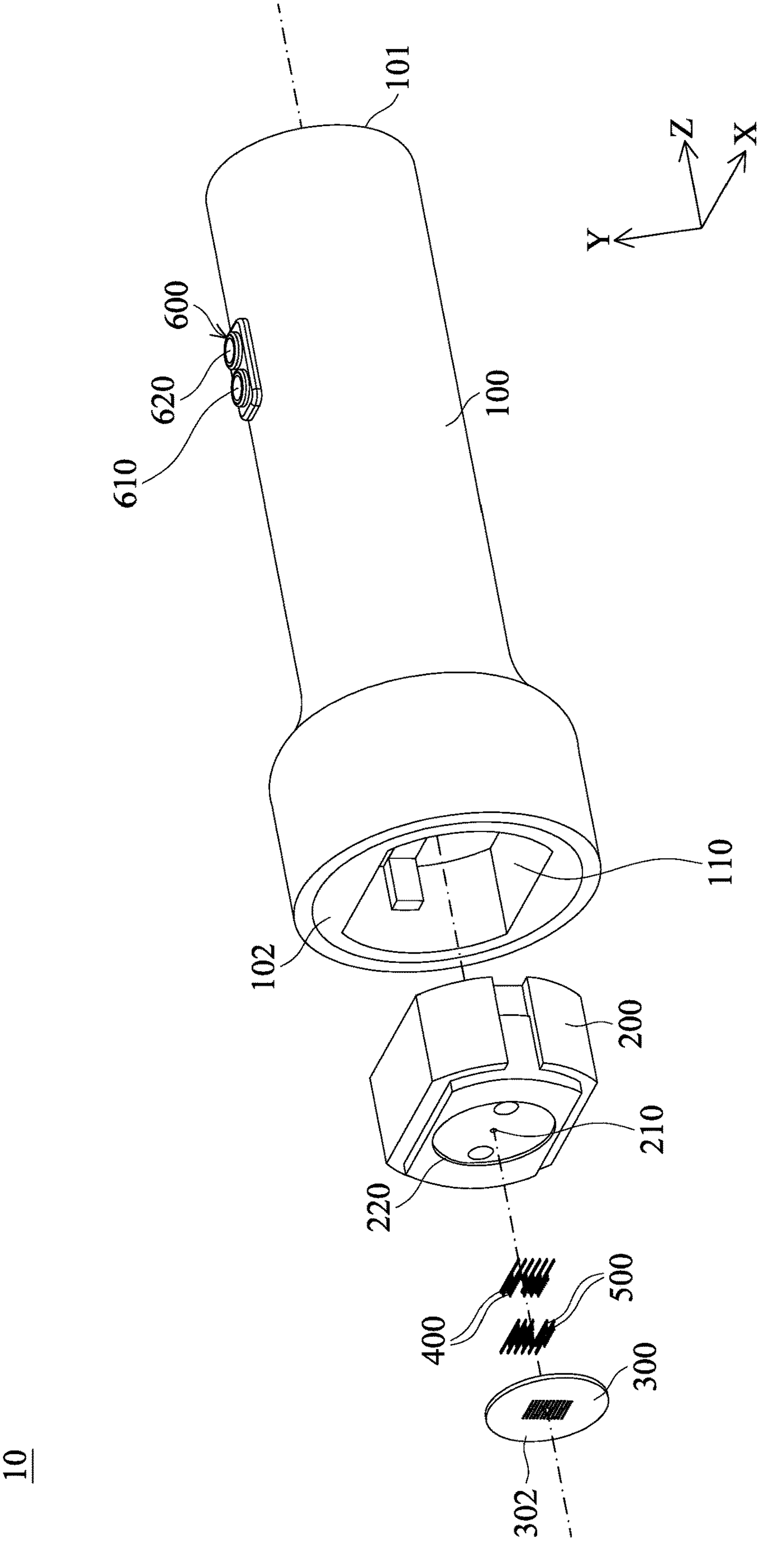
FIG. 3 is an exploded-view diagram of the microneedle electroporation device according to an embodiment of the invention.

Referring to FIG. 2 and FIG. 3, the microneedle electroporation device 10 primarily includes a housing 100, a positioning member 200, an intermediate plate 300, a plurality of first microneedle assemblies 400, a plurality of second microneedle assemblies 500, a socket 600, a first wire W1, and a second wire W2.

The housing 100 has an accommodating space 110 extending from an end 101 of the housing 100 to another end 102. The positioning member 200 is disposed in the accommodating space 110, and adjacent to the end 102 of the housing 100. In this embodiment, the positioning member 200 includes a pin hole 210, and a receiving recess 220 is formed on the surface of the positioning member 200 facing away the accommodating space 110.

When the microneedle electroporation device 10 is assembled, the intermediate plate 300 is accommodated in the receiving recess 220 of the positioning member 200. Since the appearance and the dimensions of the receiving recess 220 are substantially the same as that of the intermediate plate 300, the intermediate plate 300 can be positioned by the receiving recess 220.

Figure 4A:
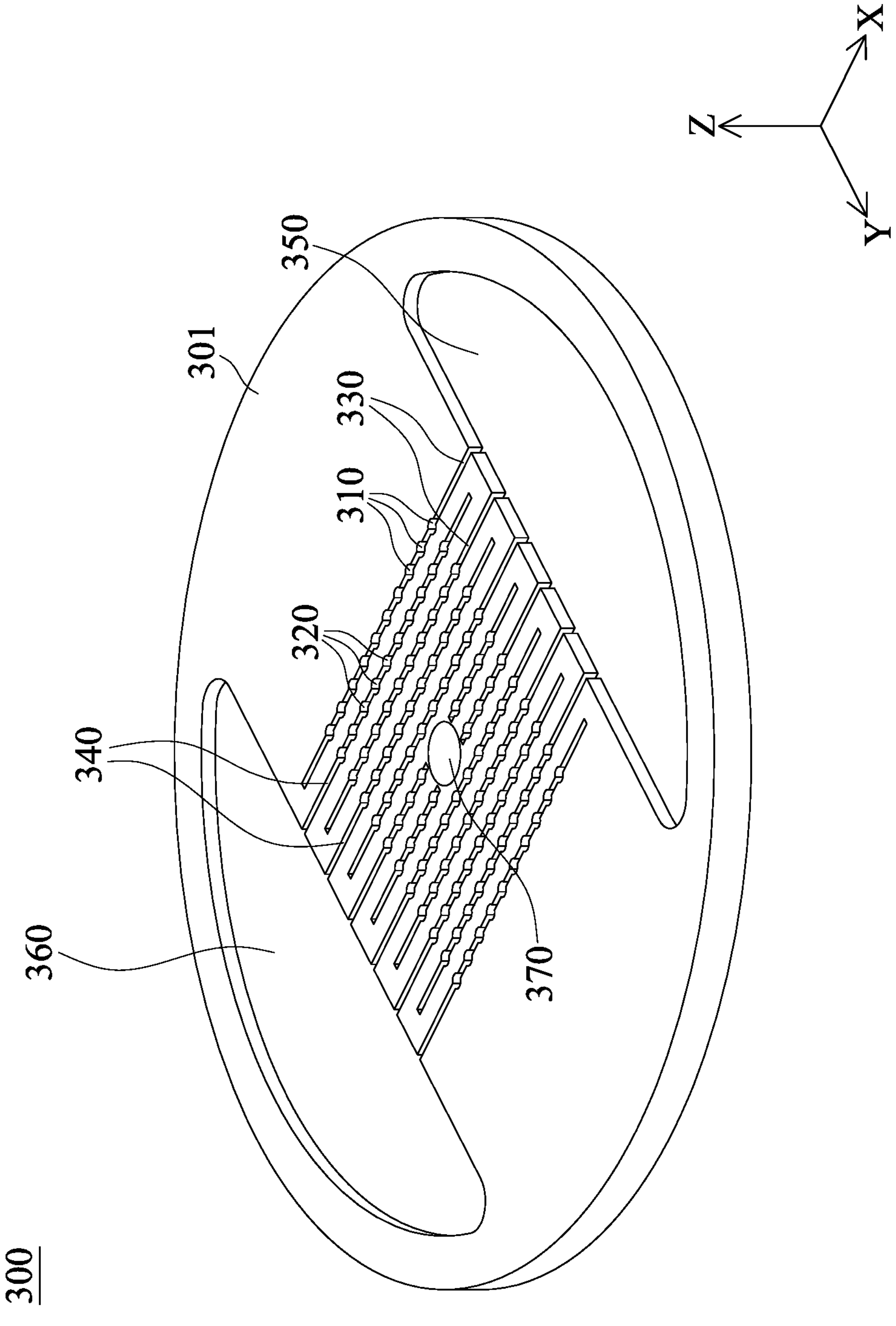
FIG. 4A is a schematic diagram of an intermediate plate according to an embodiment of the invention.
Figure 4B:
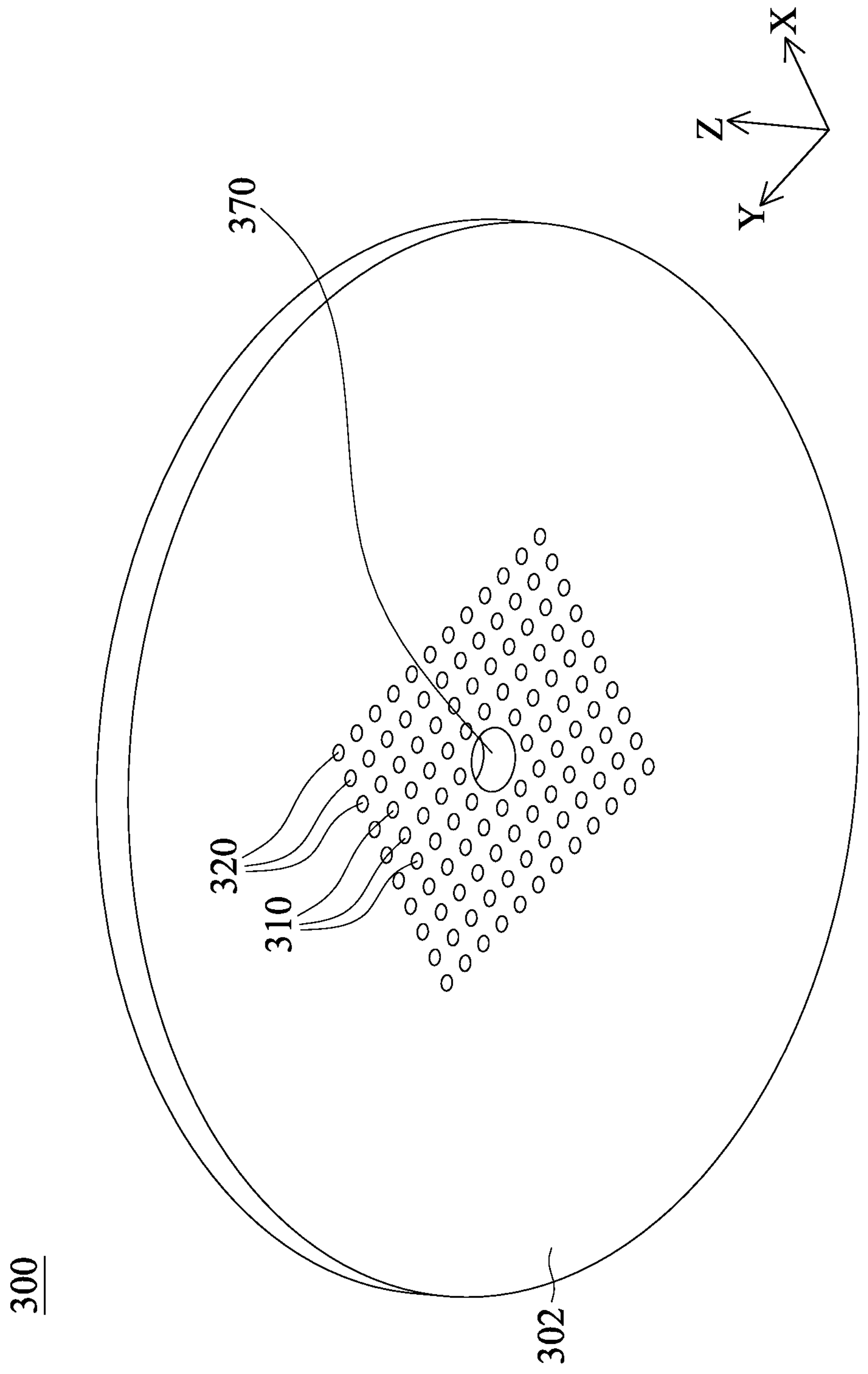
FIG. 4B is a schematic diagram of the intermediate plate in another view according to an embodiment of the invention.

As shown in FIG. 4A and FIG. 4B, the intermediate plate 300 includes a first surface 301, a second surface 302, a plurality of first holes 310, a plurality of second holes 320, a plurality of first slots 330, a plurality of second slots 340, a first depression portion 350, and a second depression portion 360, wherein the first surface 301 is opposite to the second surface 302.

In this embodiment, the first holes 310 and the second holes 320 penetrate the intermediate plate from the first surface 301 to the second surface 302, and are arranged on the intermediate plate 300 in a matrix manner. In the X-axis, the plurality of the first holes 310 are adjacently arranged, and the plurality of the second holes are adjacently arranged. In the Y-axis, the first holes 310 and the second holes 320 are arranged in a staggered arrangement.

The first slots 330, the second slots 340, the first depression portion 350, and the second depression portion 360 are formed on the first surface 301, and the first holes 310 and the second holes 320 are disposed between the first depression portion 350 and the second depression portion 360. The first slots 330 connect the plurality of first holes 310 along the X-axis, and is communicated with the first depression portion 350. In this embodiment, the first slots 330 are parallel to each other. The second slots 340 connect the plurality of second holes 320 along the X-axis, and is communicated with the second depression portion 360. In this embodiment, the second slots 340 are parallel to each other. It should be noted that, the first slots 330 are separated from the second depression portion 360, the second slots 340 are separated from the first depression portion 350, and the first slots 330 are separated from the second slots 340. In other words, the first slots 330 are not communicated with the second slots 340 and the second depression portion 360, and the second slots 340 are not communicated with the first slots 330 and the first depression portion 350.

The intermediate plate 300 further includes a through hole 370. The through hole 370 penetrates the intermediate plate from the first surface 301 to the second surface 302, and located at the center of the intermediate plate 300. In this embodiment, the dimensions (the cross-sectional area) of each of the first holes 310 are substantially the same as the dimensions (the cross-sectional area) of each of the second holes 320, and the dimensions (the cross-sectional area) of the through hole 370 is larger than the dimensions (the cross-sectional area) of each of the first holes 310 and the dimensions (the cross-sectional area) of each of the second holes 320.

Figure 5A:
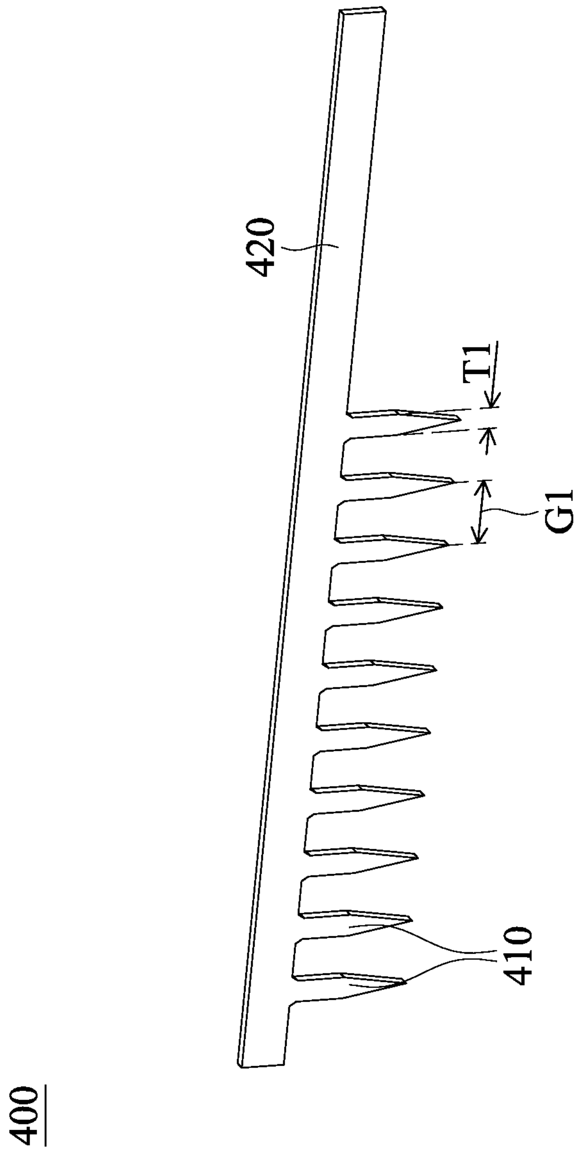
FIG. 5A is a schematic diagram of a first microneedle assembly according to an embodiment of the invention.
Figure 5B:
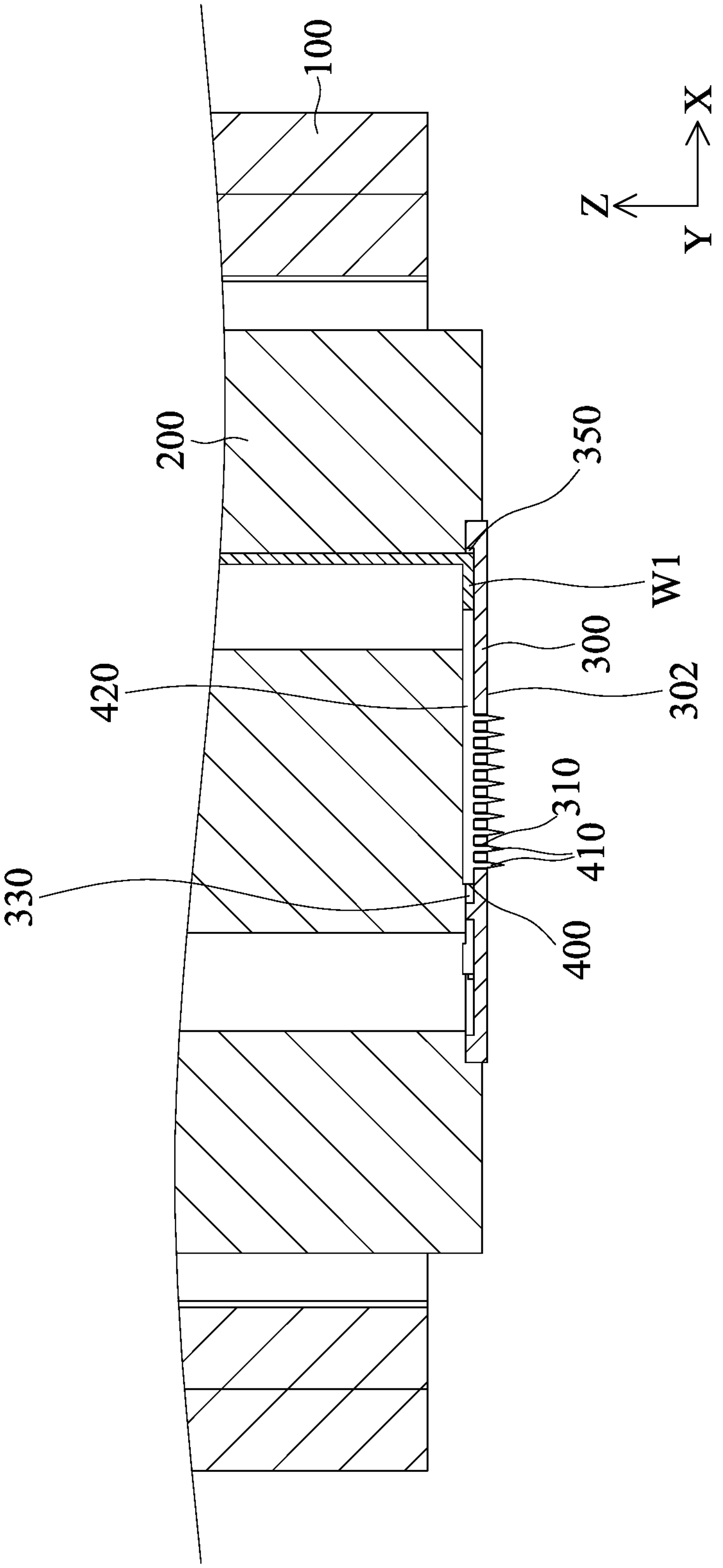
FIG. 5B is a partial cross-sectional view of the microneedle electroporation device according to an embodiment of the invention.

Referring to FIG. 5A and FIG. 5B, each of the first microneedle assemblies 400 includes a plurality of first microneedles 410 and a first metal connecting portion 420.

When the microneedle electroporation device 10 is assembled, the first microneedle assemblies 400 are disposed between the intermediate plate 300 and the positioning member 200, the first microneedles 410 pass through the first holes 310 and protrude from the second surface 302 of the intermediate plate, and the first metal connecting portions 420 are accommodated in the first slots 330. In this embodiment, a portion of each of the first metal connecting portions 420 is accommodated in the first depression portion 350, and the first wire W1 is electrically connected to the first metal connecting portions 420 of the plurality of the first microneedle assemblies 400 in the first depression portion 350.

Figure 6A:
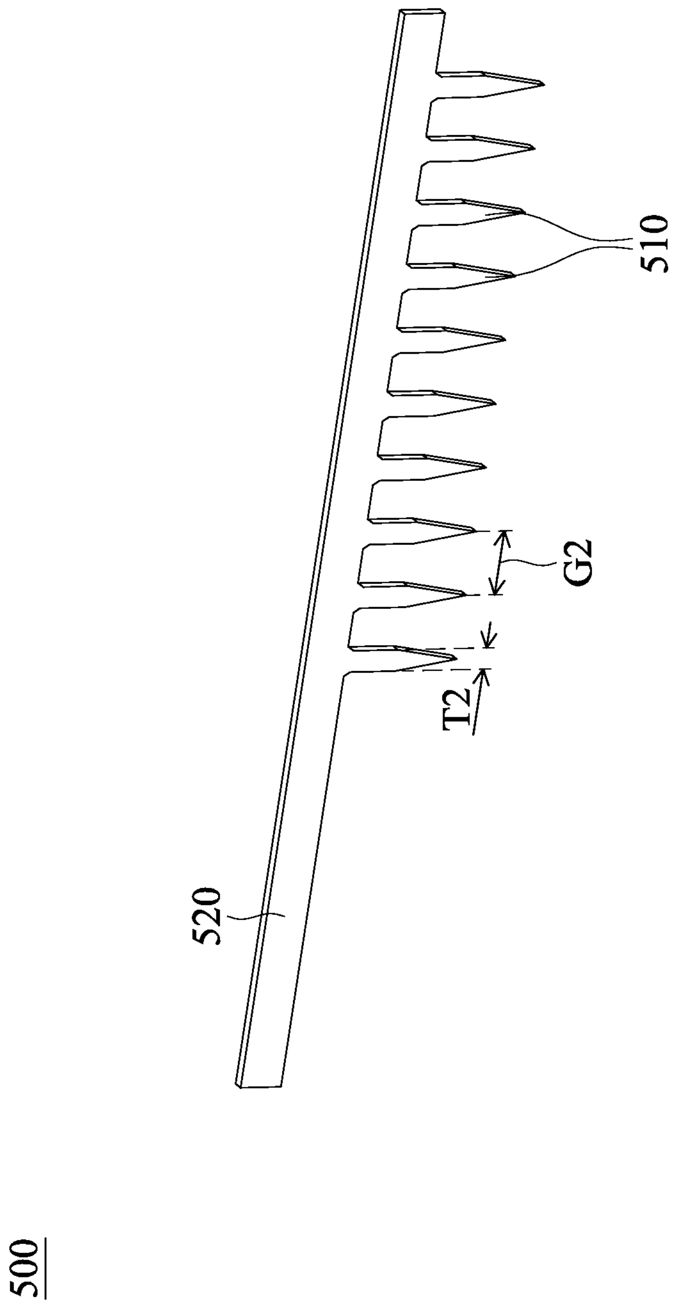
FIG. 6A is a schematic diagram of a second microneedle assembly according to an embodiment of the invention.
Figure 6B:
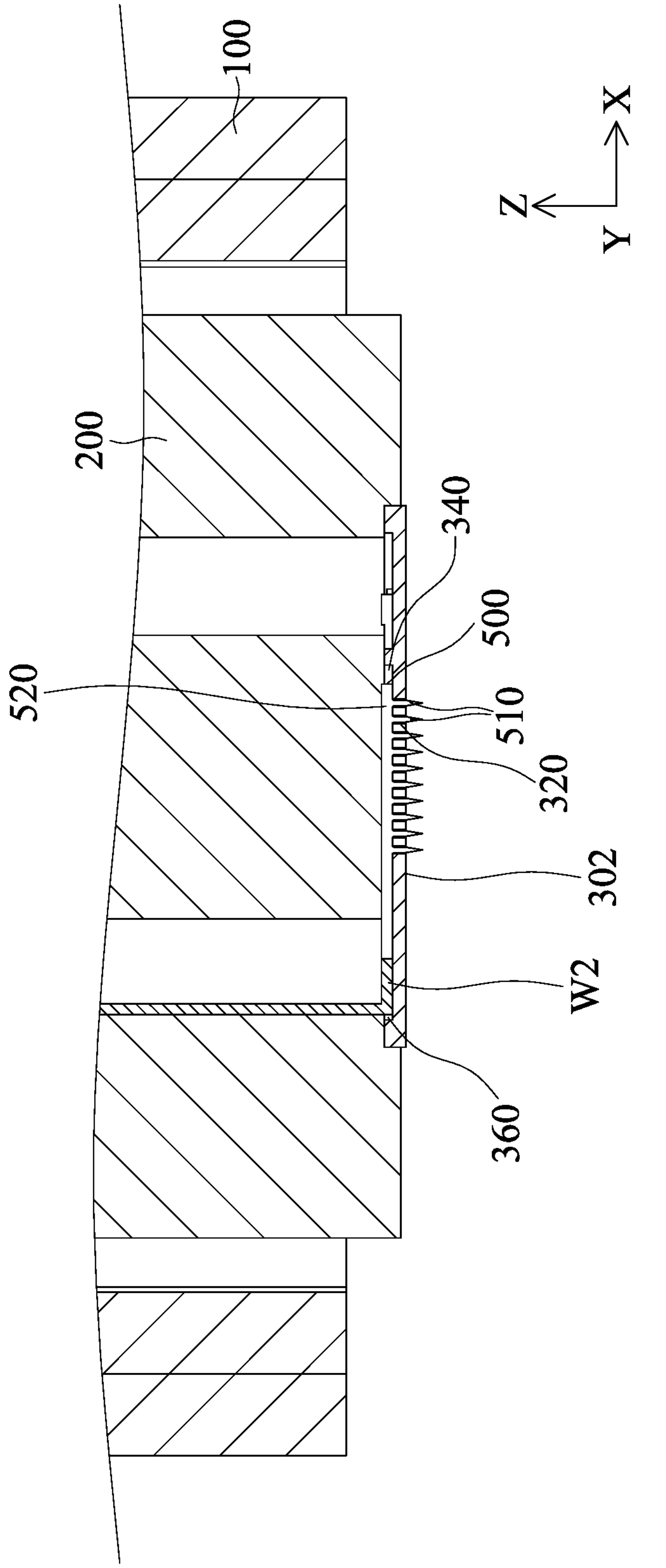
FIG. 6B is a partial cross-sectional view of the microneedle electroporation device according to an embodiment of the invention.

Referring to FIG. 6A and FIG. 6B, similar to the first microneedle assemblies 400, each of the second microneedle assemblies 500 includes a plurality of second microneedles 510 and a second metal connecting portion 520. When the microneedle electroporation device 10 is assembled, the second microneedle assemblies 500 are disposed between the intermediate plate 300 and the positioning member 200, the second microneedles 510 pass through the second holes 320 and protrude from the second surface 302 of the intermediate plate 300, and the second metal connecting portions 520 are accommodated in the second slots 340. In this embodiment, a portion of each of the second metal connecting portions 520 is accommodated in the second depression portion 360, and the second wire W2 is electrically connected to the second metal connecting portions 520 of the plurality of the second microneedle assemblies 500 in the second depression portion 360. Referring to FIG. 5B and FIG. 6B, the partial or the whole surface of the first depression portion 350 can include a conductive layer to electrically connect the first microneedle assembly 400 to the first wire W1, and the partial or the whole surface of the second depression portion 360 can include a conductive layer to electrically connect the second microneedle assembly 500 to the second wire W2.

Since the first holes 310 and the second holes 320 are arranged in in a staggered arrangement in the Y-axis, the first slots 330 and the second slots 340 are formed on the intermediate plate 300 in a parallel and staggered arrangement. Therefore, the first microneedle assemblies 400 and the second microneedle assemblies are arranged on the intermediate plate 300 in a staggered arrangement too, and the first metal connecting portions 420 and the second metal connecting portions 520 are parallel to each other.

Figure 6C:
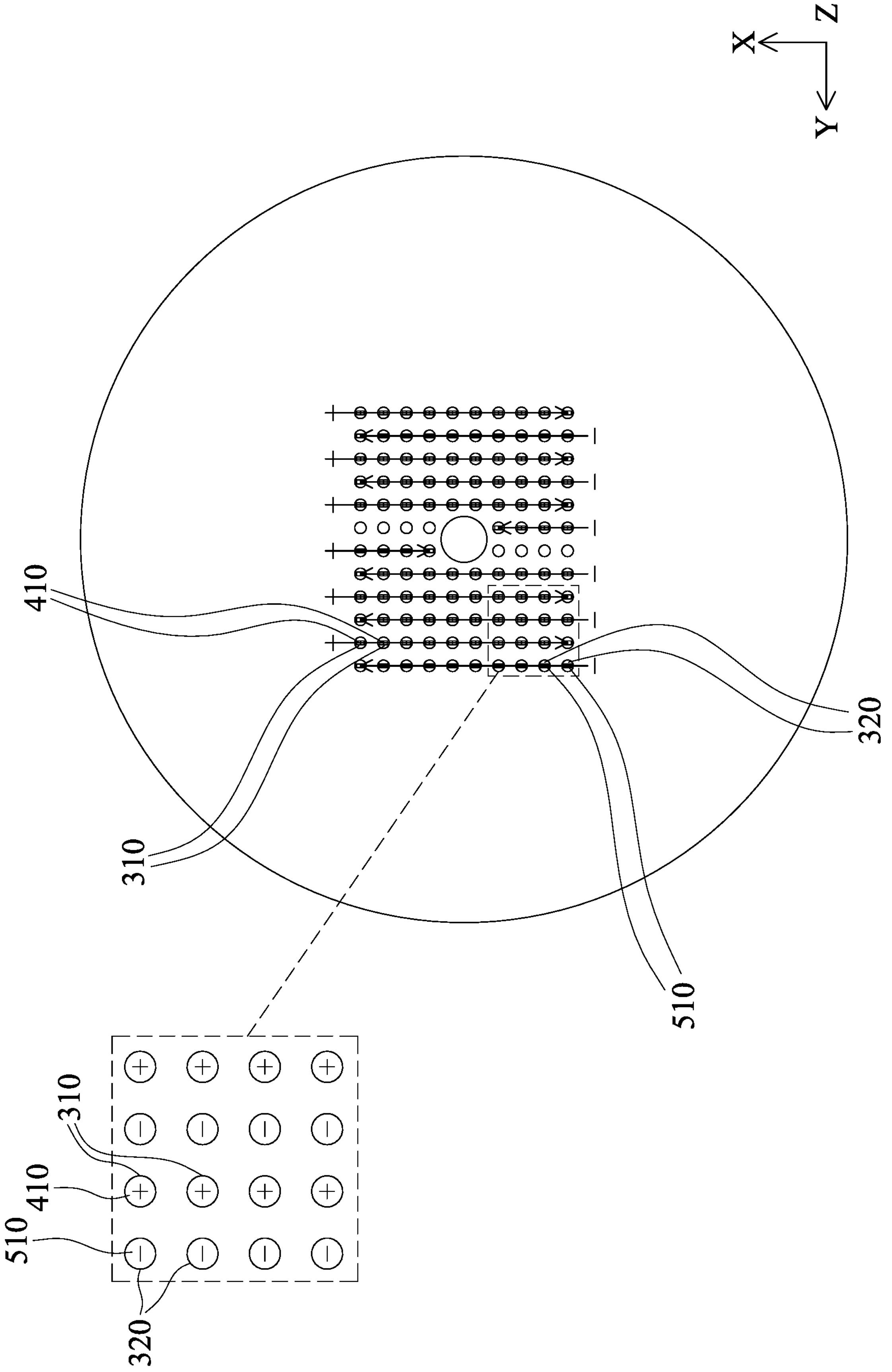
FIG. 6C is a schematic diagram that represents that an external power feeding device produces poles on the microneedle electroporation device according to an embodiment of the invention.

Referring to FIG. 2, in this embodiment, the socket 600 is disposed on the housing 100, and can be electrically connected to the external power feeding device. In particular, the socket 600 includes two inserting holes 610 and 620. The inserting hole 610 is electrically connected to the first microneedle assemblies 400 via the first wire W1, and the inserting hole 620 is electrically connected to the second microneedle assemblies 500 via the first wire W2. The external power feeding device can apply a bias voltage through the inserting holes 610 and 620, and produce an electric field between the first microneedles 410 and the second microneedles 510. For example, as shown in FIG. 6C, the external power feeding device can form a positive pole on the first microneedles 410 of the first microneedle assemblies 400 via the first wire W1, and form a negative pole on the second microneedles 510 of the second microneedle assemblies 500 via the second wire W2.

Figure 7A:
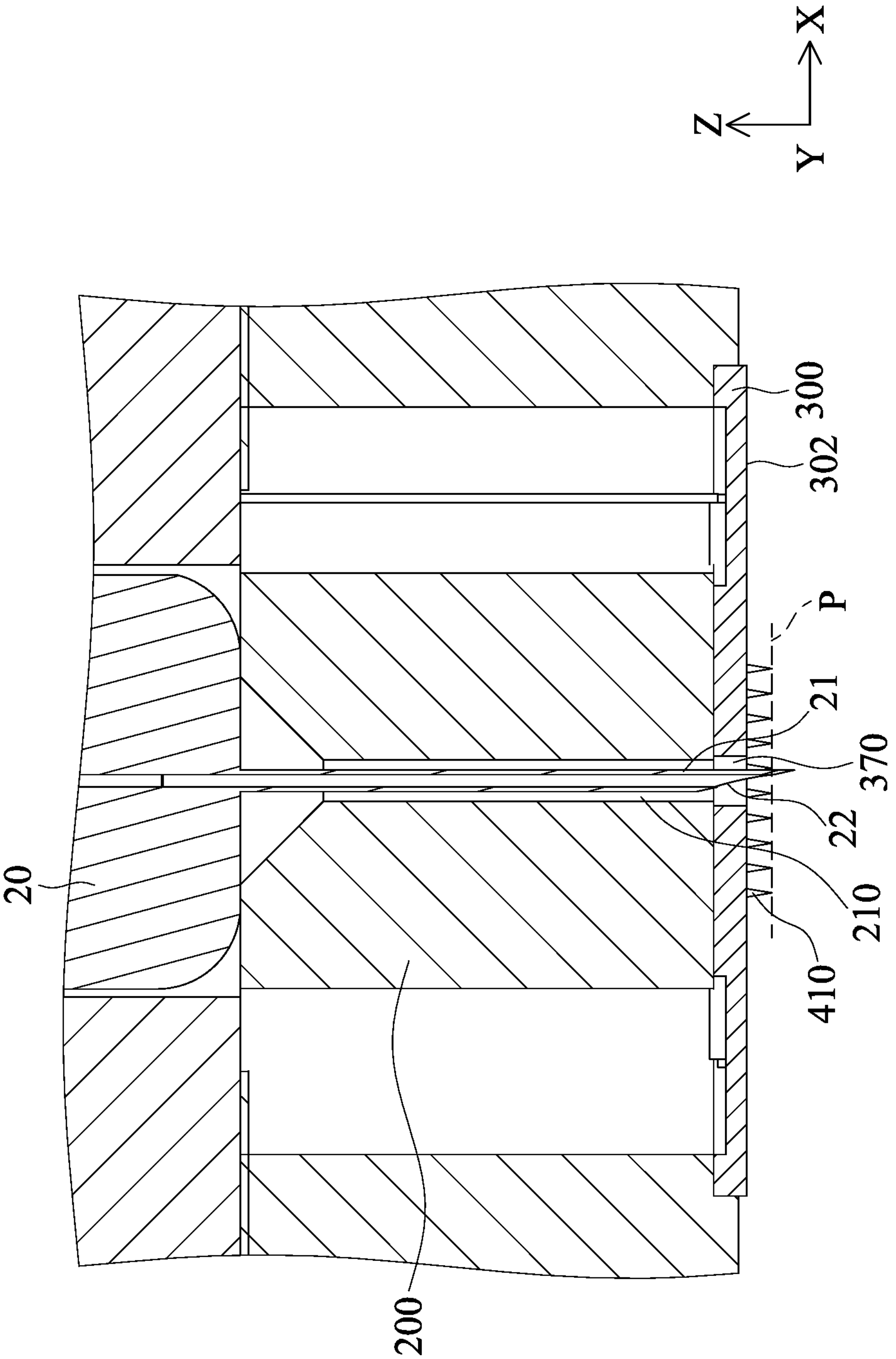
FIG. 7A is a schematic diagram of the microneedle electroporation device connected to the injecting device according to an embodiment of the invention.
Figure 7B:
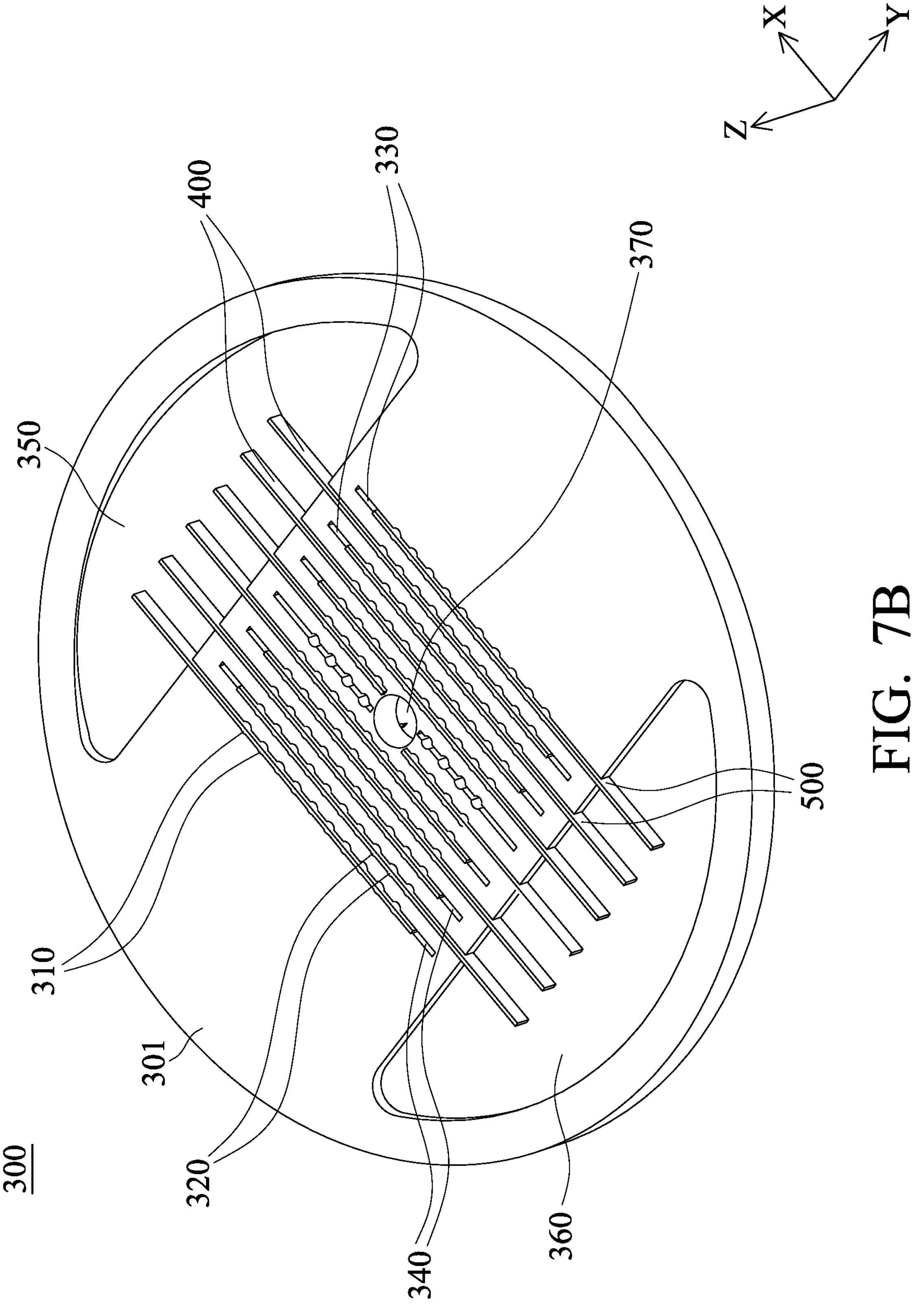
FIG. 7B is a schematic diagram of the first microneedle assemblies, the second microneedle assemblies, and the intermediate plate according to an embodiment of the invention.

As shown in FIG. 7A, when the injecting device 20 enters the accommodating space 110 of the housing 100 and connects to the microneedle electroporation device 10, the needle head 21 of the injecting device 20 passes through the through hole 370 on the intermediate plate 300, and the injecting device 20 is in contact with the positioning member 200 and/or the housing 100 to position the opening 22 of the needle head 21 relative to the intermediate plate 300.

In this embodiment, the length of each of the first microneedles 410 is substantially the same as the length of each of the first microneedles 510 in the Z-axis, so that theirs ends are substantially disposed on a virtual plane P. After positioning, the opening 22 of the needle head 21 of the injecting device 20 overlaps the virtual plane P. Thus, it can be ensured that when the injecting device 20 injects the liquid, the microneedle electroporation device 10 can form the electric field around the injecting position of the injecting liquid in a similar depth by the first microneedles 410 and the second microneedles 510.

In this embodiment, the first microneedles 410 and the second microneedles 510 protrude from the second surface 302 of the intermediate plate 300 about 0.03 mm-3.00 mm. Therefore, when they insert into the skin of the human, they can be substantially disposed at the epidermis to the dermis. Since there are more immune cells in this area, when the aforementioned microneedle structure applies the electric field to the cells to open the cell membranes and let the vaccine entering the cells, the immune response of the human can be increased, and the dosage of the vaccine can be reduced.

Figure 7C:
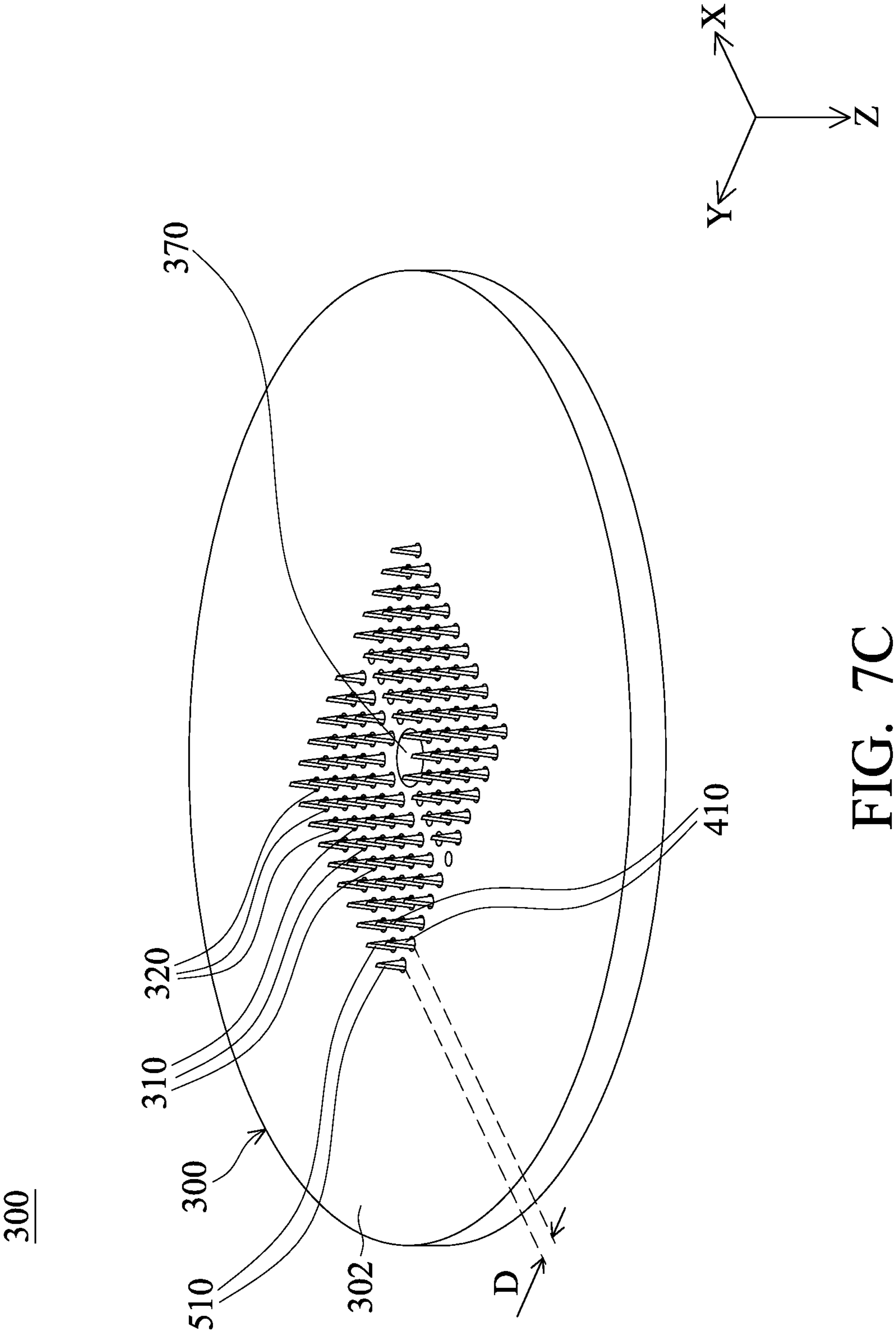
FIG. 7C is a schematic diagram of the first microneedle assemblies, the second microneedle assemblies, and the intermediate plate in another view according to an embodiment of the invention.

In this embodiment, the intermediate plate 300 includes ceramic material, and the first microneedle assemblies 400 and the second microneedle assemblies 500 include nickel and the alloy thereof, but it is not limited thereto. In some embodiments, the intermediate plate 300 includes suitable insulating material (such as plastic, glass, or etc.), and the first microneedle assemblies 400 and the second microneedle assemblies 500 include suitable conductive material (such as gold, copper, iron, platinum, or other metal material) or a structure with a conductive layer covered on the insulating material. The first microneedles 410 and the first metal connecting portion 420 can be integrally formed in one piece, for example, by electroforming. The second microneedles 510 and the second metal connecting portion 520 can be integrally formed in one piece, for example, by electroforming. In an embodiment, referring to FIG. 5A and FIG. 6A, the width T1 of each of the first microneedles 410 and the width T2 of each of the microneedles 420 are ranged in 50 um-500 um. The gap G1 between the first microneedles 410 and the gap G2 between the second microneedles 510 respectively correspond to the gap between the first holes 310 in the same slot of the intermediate plate 300 and the gap between the second holes 320 in the same slot of the intermediate plate 300. In an embodiment, the aforementioned gaps are arranged in 50 um-1000 um. The microneedles can be easily inputted into the holes by the corresponding gaps. Referring to FIG. 7C, the distance D between the first microneedles 410 and the second microneedles 510 is determined by the distance between the first holes 310 and the second holes 320. The aforementioned distance can be adjusted according to the required electric field, the voltage desired to apply (for example, less than 100V), and the position where the electroporation is applied on. In the smaller distance, the voltage required to achieve the same electric field can be effectively reduced. In an embodiment, the distance D is ranged in 50 um-1000 um. The number of microneedle arrays formed by the first microneedles 410 and the second microneedles 510 can be determined by the numbers of the first slot 330, the second slots 340, the first holes 310 and the second holes 320 on the intermediate plate 300. For example, in FIG. 4A and FIG.

4B, the intermediate plate 300 includes six first slots 330 and six second slots 340, and there are ten holes in each of the slots. 12×10 hole arrays can be therefore formed. The number of the microneedles on each of the microneedle assemblies can be corresponded to the number of the holes, or disposed in part of the holes. When the microneedles are disposed, 12×10 microneedle arrays are formed. Since the through hole 370 in the embodiment is situated at the center of the intermediate plate 300, parts of the first and second slots are not continuous, and the number of the microneedles on some microneedle assemblies should be reduced. Thus, the number of the microneedles in the microneedle arrays can be easily changed by the different numbers of the microneedles, the slots, and holes on the intermediate plate.

After assembled, the positioning member 200, the intermediate plate 300, the first microneedle assemblies 400, and the second microneedle assemblies 500 can form an integrated component having the microneedle arrays. Thus, the user can easily replace it after used. In some embodiments, the housing 100 and the positioning member 200 can be integrally formed in one piece. Moreover, the electroporation device in this embodiment can be easily engaged with the syringe in the market, so as to have the functions of injection and electroporation together.

Figure 8:
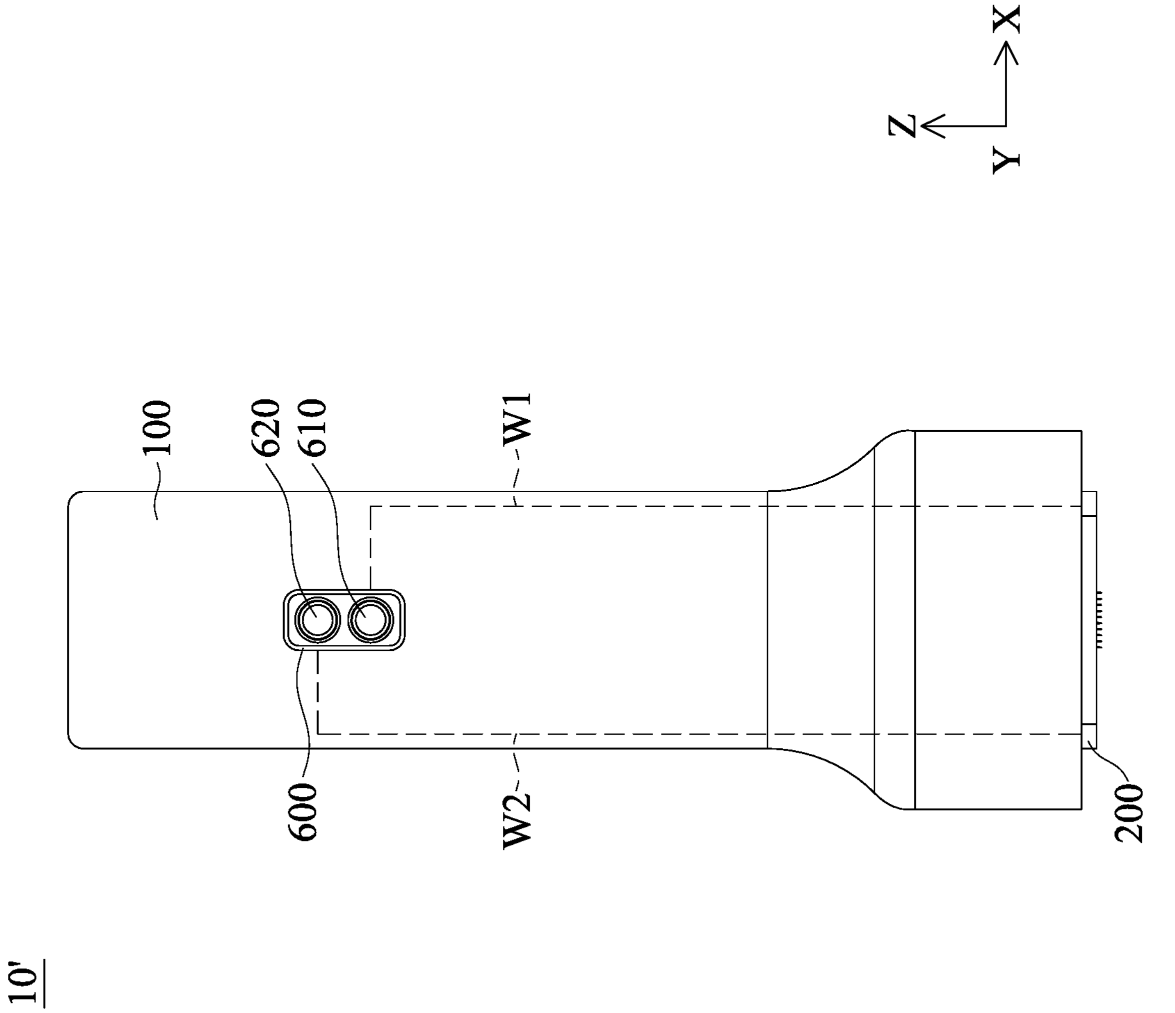
FIG. 8 is a schematic diagram of a microneedle electroporation device according to another embodiment of the invention.
Figure 9:
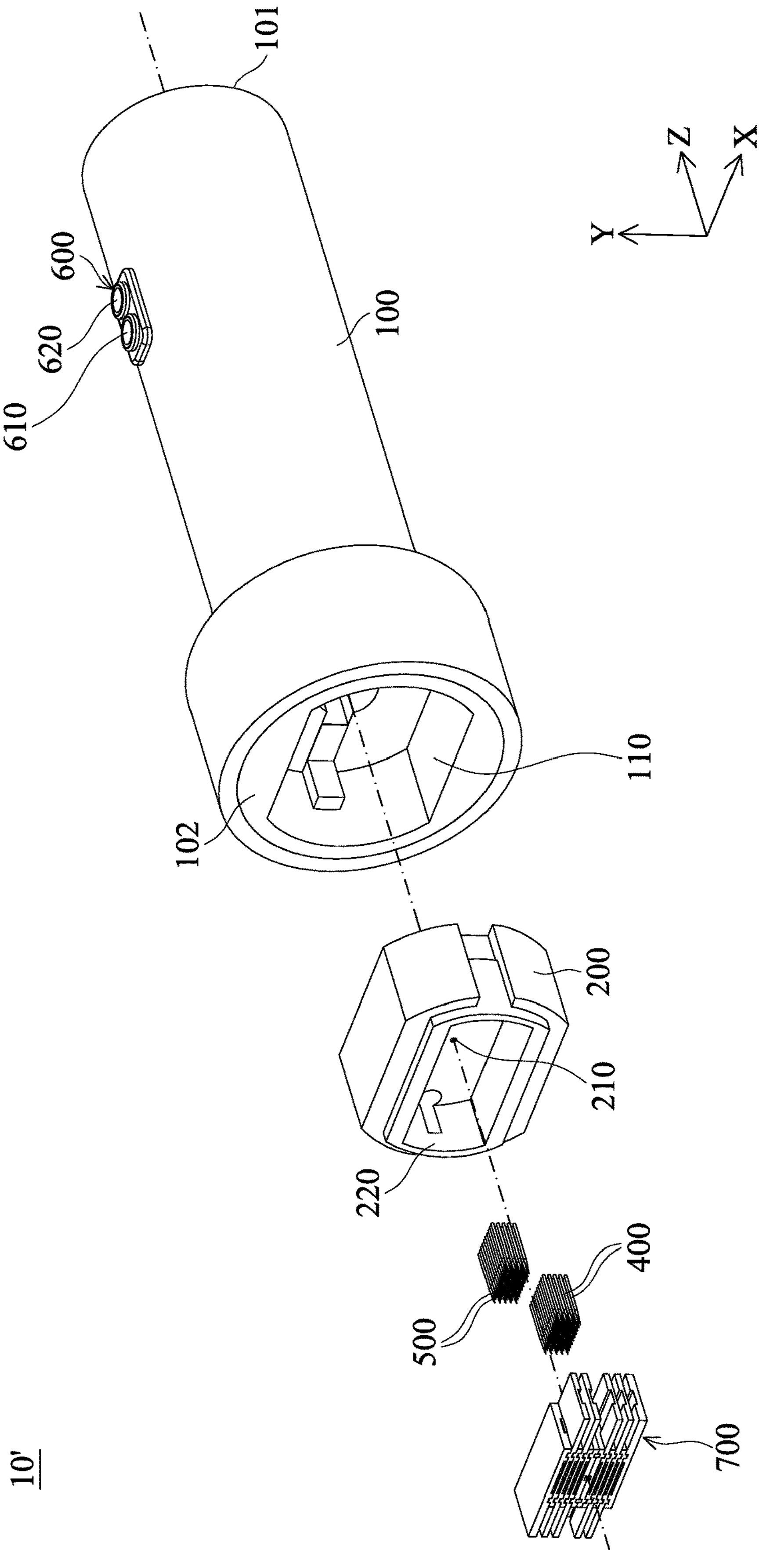
FIG. 9 is an exploded-view diagram of the microneedle electroporation device according to another embodiment of the invention.

Referring to FIG. 8 and FIG. 9, a microneedle electroporation device 10' in another embodiment of the invention primarily includes a housing 100, a positioning member 200, a plurality of first microneedle assemblies 400, a plurality of second microneedle assemblies 500, a socket 600, a first wire W1, a second wire W2, and an intermediate module 700.

The housing 100 have an accommodating space 110, and the accommodating space 110 is extended from an end 101 of the housing 100 to another end 102. The positioning member 200 is disposed in the accommodating space 110, and adjacent to the end 102 of the housing 100. In this embodiment, the positioning member 200 includes a pin hole 210, and a receiving recess 220 is formed on the surface of the positioning member 200 facing away the accommodating space 110.

Figure 10A:
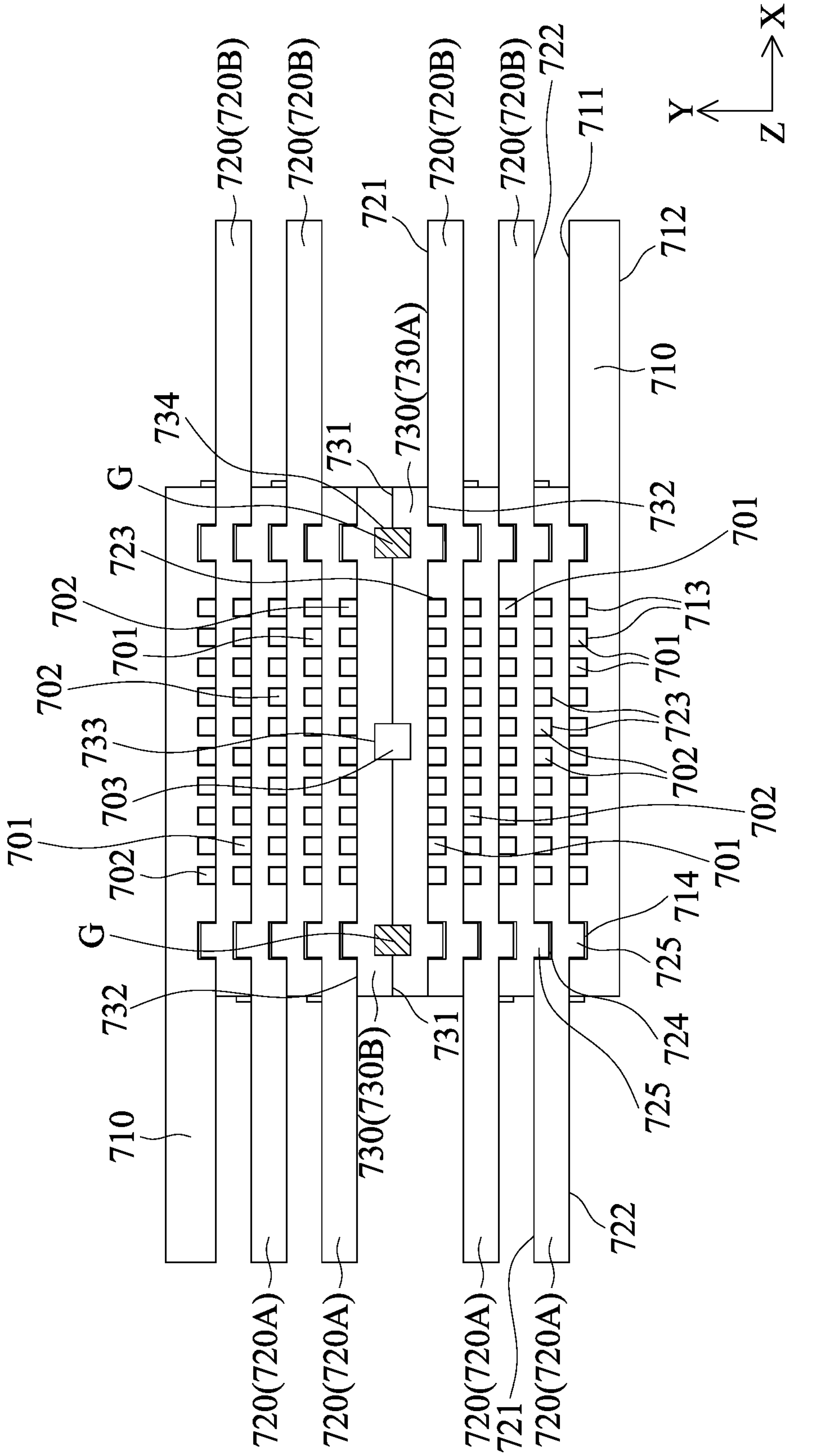
FIG. 10A is a schematic diagram of an intermediate module according to another embodiment of the invention.

When the microneedle electroporation device 10' is assembled, the intermediate module 700 is accommodated in the receiving recess 220 of the positioning member 200. As shown in FIG. 10A, the intermediate module 700 is formed by a plurality of stacked plates. In this embodiment, the plates includes one or more first plates 710, one or more second plates 720, and one or more third plates 730. These plates cane be the semiconductor substrates (such as the silicon substrates) or the insulation substrates (such as glass, plastic, polymer material, or etc.).

Figure 10B:
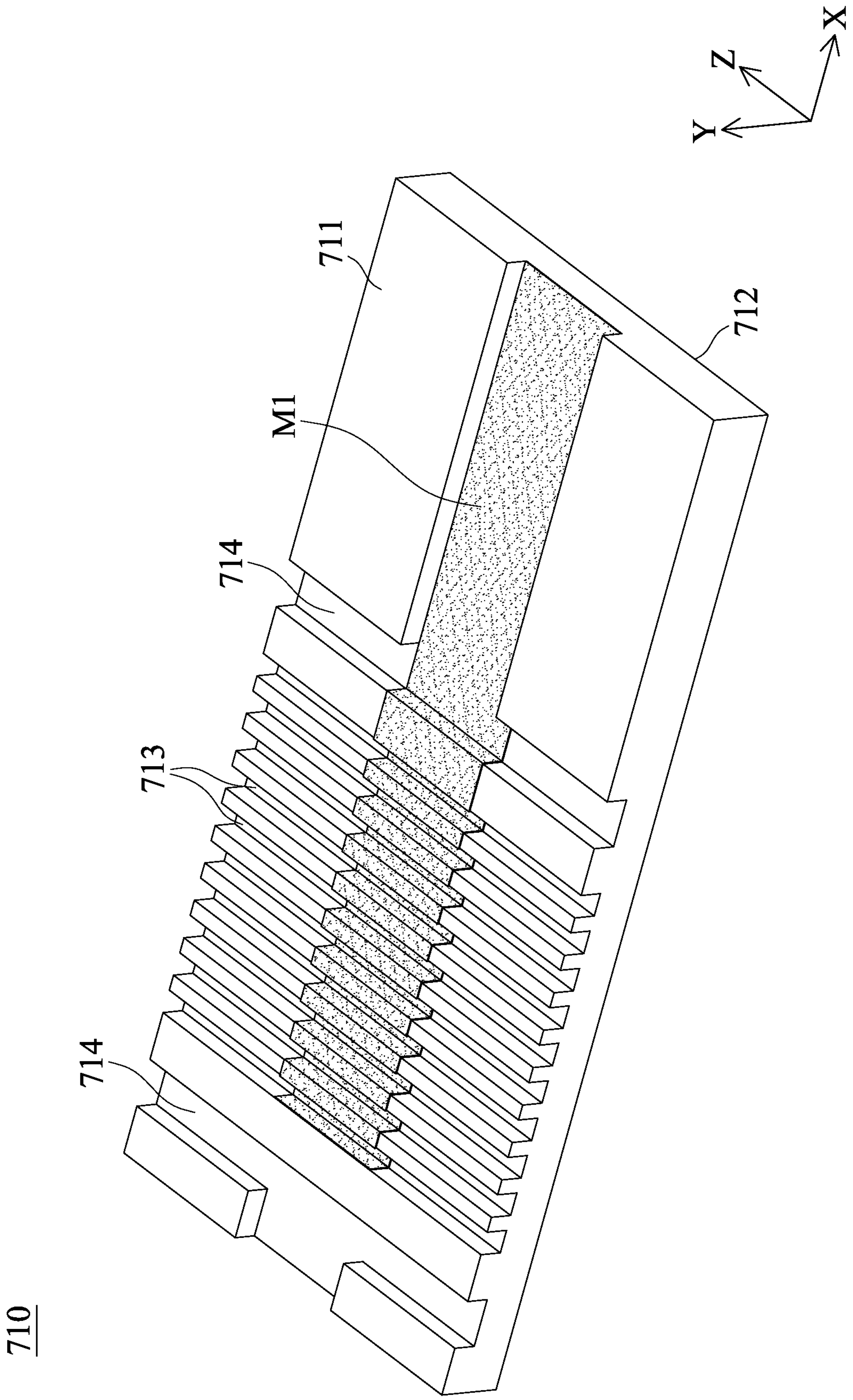
FIG. 10B is a schematic diagram of a first plate according to another embodiment of the invention.

Referring to FIG. 10B, the first plate 710 has a first top surface 711 and a first bottom surface 712, and a plurality of first grooves 713 parallel to each other and at least one positioning groove 714 are formed on the first top surface 711. For example, the positioning groove 714 can include a T-shaped cross-section or an L-shaped cross-section. Furthermore, a first metal plating film M1 is disposed on the first top surface 711. The first metal plating film M1 is disposed on partial surface of the positioning groove 714, extended along the X-axis and enters each of the first grooves 713. In this embodiment, the first metal plating film M1 is attached to partial inner walls of each of the first grooves 713. The surfaces of the first top surface 711 and the first bottom surface 712 can include an insulation layer, and the first metal plating film M1 is disposed on the insulation layer.

Figure 10C:
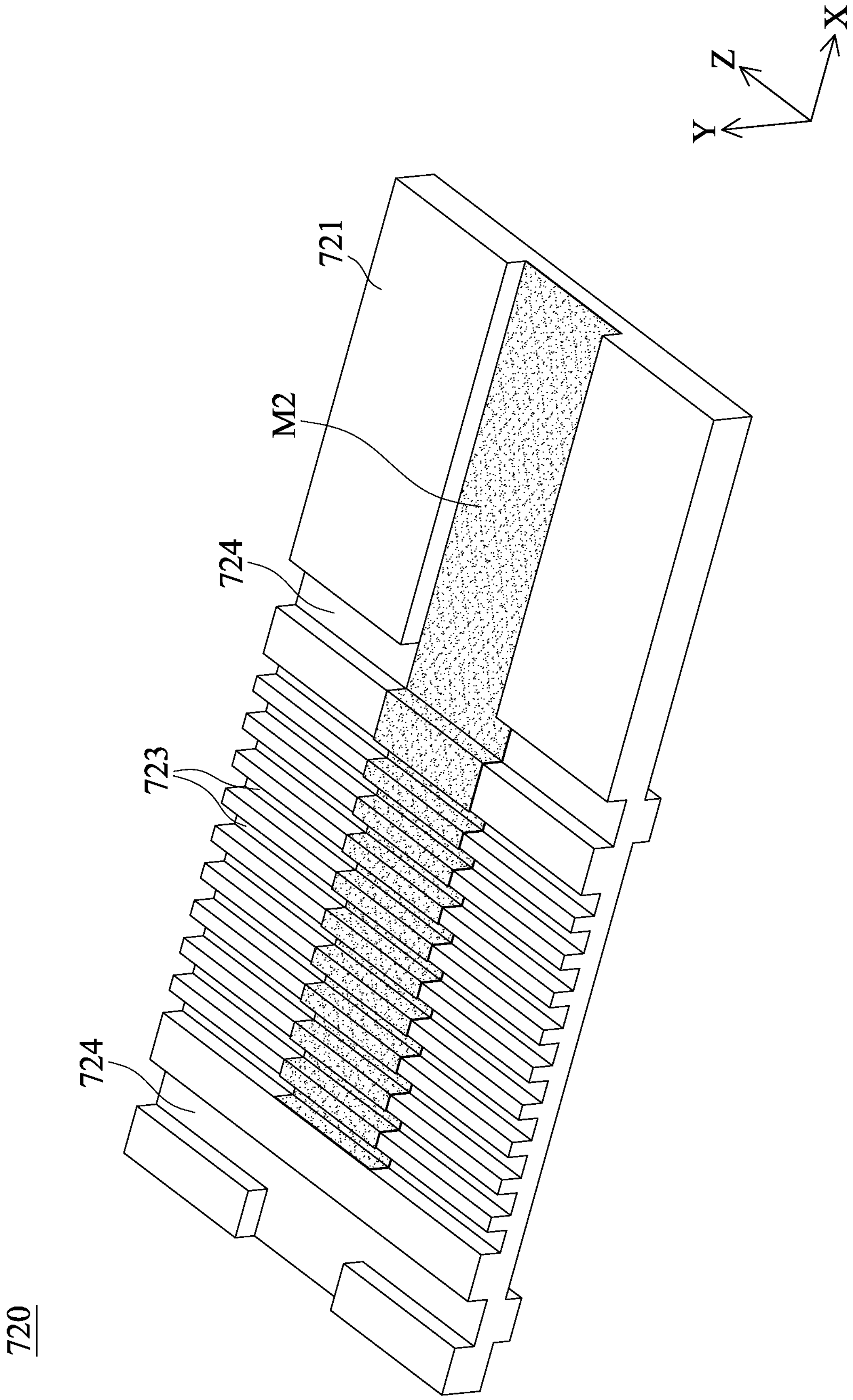
FIG. 10C is a schematic diagram of a second plate according to another embodiment of the invention.
Figure 10D:
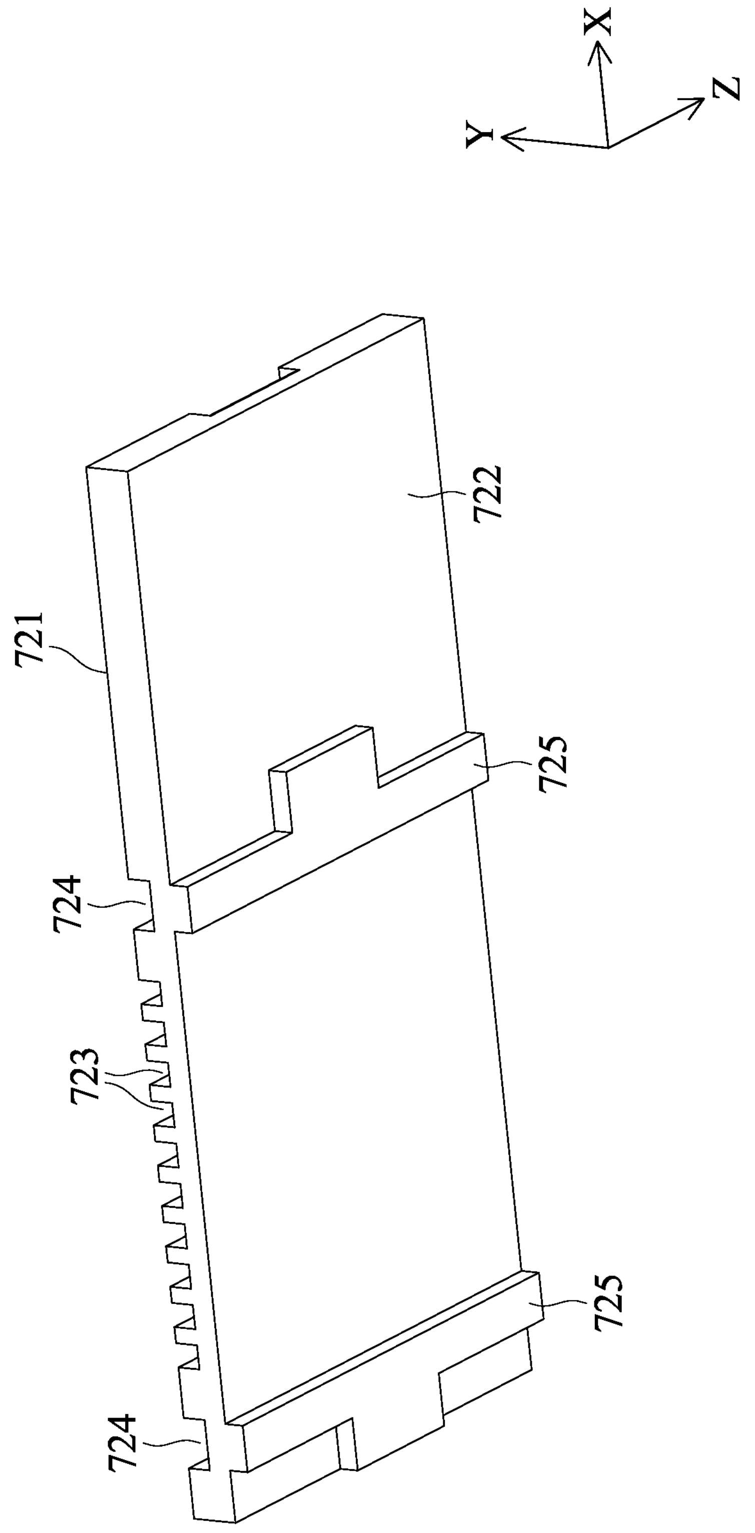
FIG. 10D is a schematic diagram of the second plate in another view according to another embodiment of the invention.

Referring to FIG. 10C and FIG. 10D, the second plate 720 has a second top surface 721 and a second bottom surface 722. A plurality of second grooves 723 parallel to each other and at least one positioning groove 724 are formed on the second top surface 721, and at least one positioning protrusion 725 is formed on the second bottom surface 722. For example, the positioning groove 724 can include a T-shaped cross-section or an L-shaped cross-section, and the appearance of the positioning protrusion 725 corresponds to the appearance of the positioning groove 714 and/or 724. In this embodiment, the appearance of the positioning groove 714 is the same as the appearance of the positioning groove 724. Furthermore, a second metal plating film M2 is disposed on the second top surface 721. The second metal plating film M2 is disposed on partial surface of the positioning groove 724, extended along the X-axis and enters each of the second grooves 723. In this embodiment, the second metal plating film M2 is attached to partial inner walls of each of the second grooves 723. The surfaces of the second top surface 721 and the second bottom surface 722 can include an insulation layer, and the second metal plating film M2 is disposed on the insulation layer.

Figure 10E:
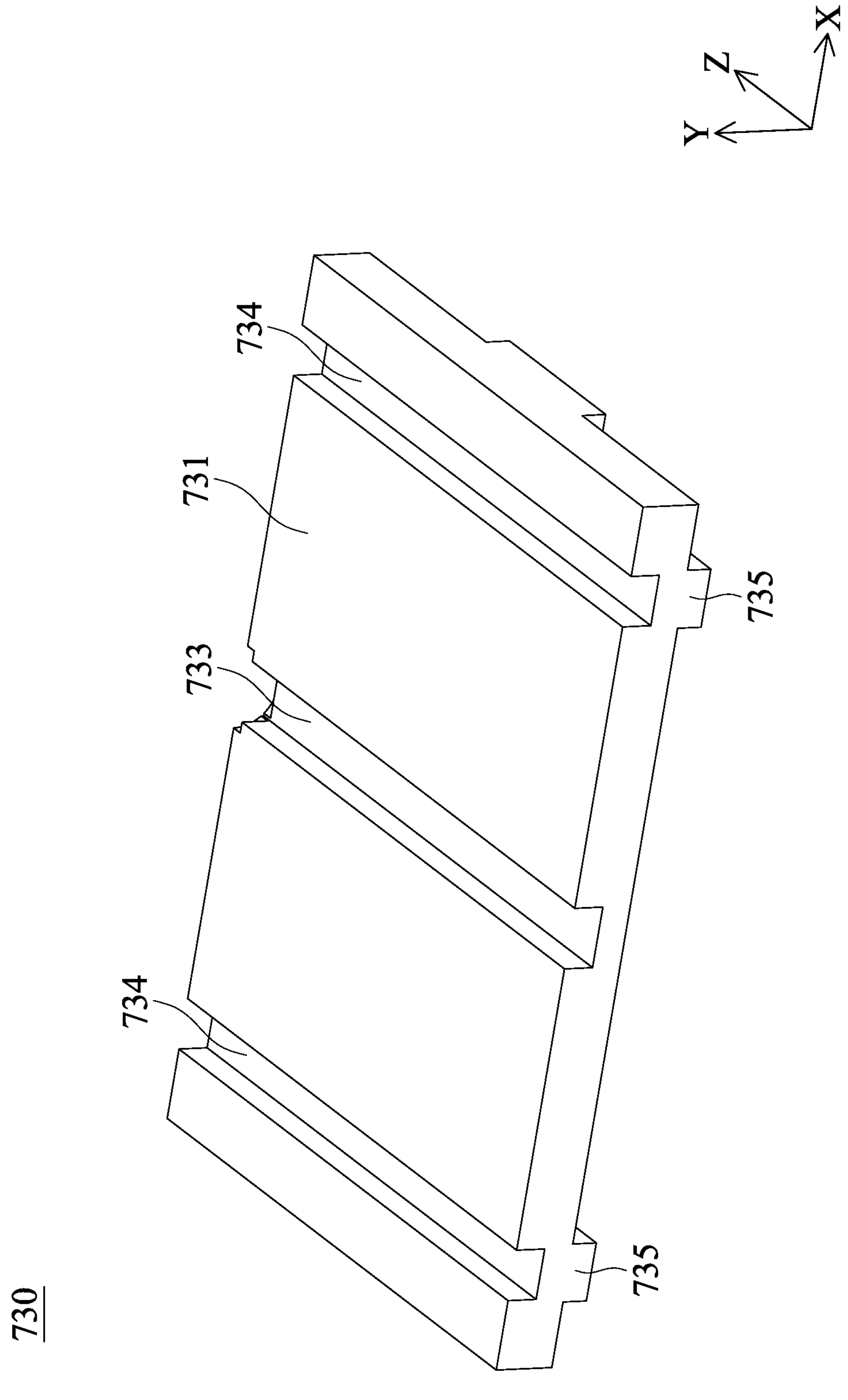
FIG. 10E is a schematic diagram of a third plate according to another embodiment of the invention.
Figure 10F:
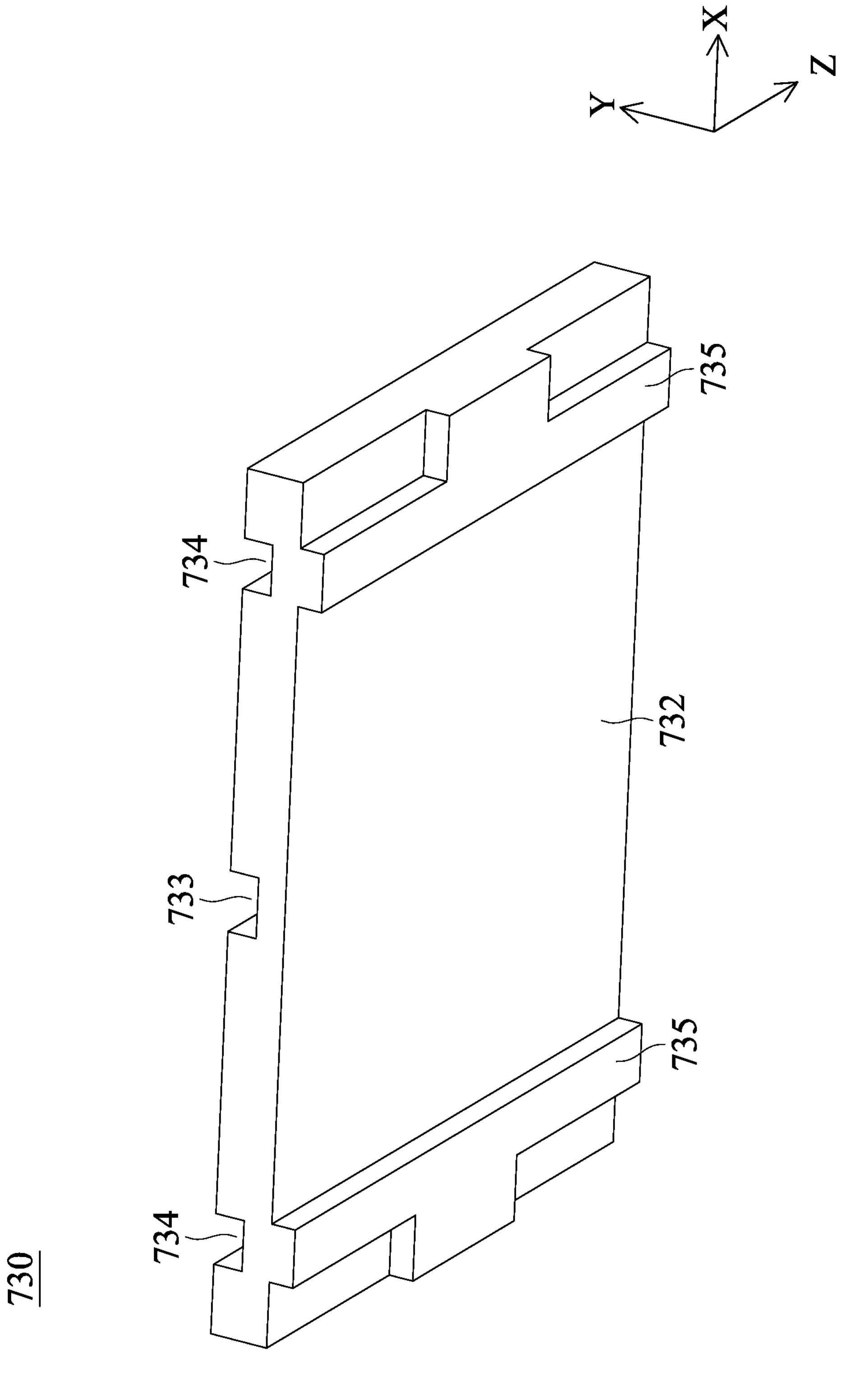
FIG. 10F is a schematic diagram of the third plate in another view according to another embodiment of the invention.

Referring to FIG. 10E and FIG. 10F, the third plate 730 has a third top surface 731 and a third bottom surface 732. A third groove 733 and at least one positioning groove 734 are formed on the first top surface 731, and at least one positioning protrusion 735 is formed on the second bottom surface 722. The appearance of the positioning protrusion 735 corresponds to the appearance of the positioning groove 724. The surfaces of the third top surface 731 and the third bottom surface 732 also can include an insulation layer.

Referring to FIG. 10A, when the user assembles the intermediate module 700, a second plate 720A can be firstly disposed on a first plate 710. The second bottom surface 722 of the second plate 720A faces and contacts the first top surface 711 of the first plate 710. The positioning protrusion 725 of the second plate 720A enters the positioning groove 714 of the first plate 710. Since each of the positioning groove 714 and positioning protrusion 725 includes the T-shaped structure (or the L-shaped structure), the first plate 710 and the second plate 720A can be affixed relative to each other in the X-axis and the Z-axis. Moreover, since the first top surface 711 has the first grooves 713, a plurality of first holes 701 can be formed between the first plate 710 and the second plate 720A.

Subsequently, the user can dispose another second plate 720B on the second plate 720A. The second bottom surface 722 of the second plate 720B faces and contacts the second top surface 721 of the second plate 720A. The positioning protrusion 725 of the second plate 720B enters the positioning groove 724 of the second plate 720A. Since each of the positioning groove 724 and positioning protrusion 725 includes the T-shaped structure (or the L-shaped structure), the second plate 720A and the second plate 720B can be affixed relative to each other in the X-axis and the Z-axis. Moreover, since the second top surface 721 of the second plate 720A has the second grooves 723, a plurality of second holes 702 or first holes 701 can be formed between the second plate 720A and the second plate 720B. In this embodiment, the arranged orientation of the second plate 720A is opposite to that to the second plate 720B. In other words, the arranged orientation of the second plate 720B is the arranged orientation of the second plate 720A rotated 180 degrees.

After stacking the suitable number of the second plate 720 as required, the user can dispose a third plate 730A on the second plate 720. The third bottom surface 732 of the third plate 730A faces and contacts the second top surface 721 of the second plate 720. The positioning protrusion 735 of the third plate 730A enters the positioning groove 724 of the second plate 720. Since each of the positioning groove 724 and positioning protrusion 735 includes the T-shaped structure (or the L-shaped structure), the second plate 720 and the third plate 730A can be affixed relative to each other in the X-axis and the Z-axis. Moreover, since the second top surface 721 of the second plate 720 has the second grooves 723, a plurality of first holes 701 (or a plurality of second holes 702) can be formed between the second plate 720 and the third plate 730A.

After the third plate 730A is disposed, another third plate 730B can be disposed on the third plate 730A. For example, a bolt or glue G can be disposed in the positioning groove 734 of the third plate 730A and the positioning groove 734 of the third plate 730B, so as to fixedly connect the third plate 730A to the third plate 730B. The third groove 733 of the third plate 730A is aligned with the third groove 733 of the third plate 730B, and a through hole 703 is therefore formed. It should be noted that, the dimensions (the cross-sectional area) of the through hole 703 are larger than the dimensions (the cross-sectional area) of each of the first holes 701 and the dimensions (the cross-sectional area) of each of the second holes 702.

After that, the user can stack a plurality of second plates 720 on the second plate 730B by the same manner, and finally dispose another first plate 710 on the second plate 720 to finish the assemble of the intermediate module 700.

Figure 11:
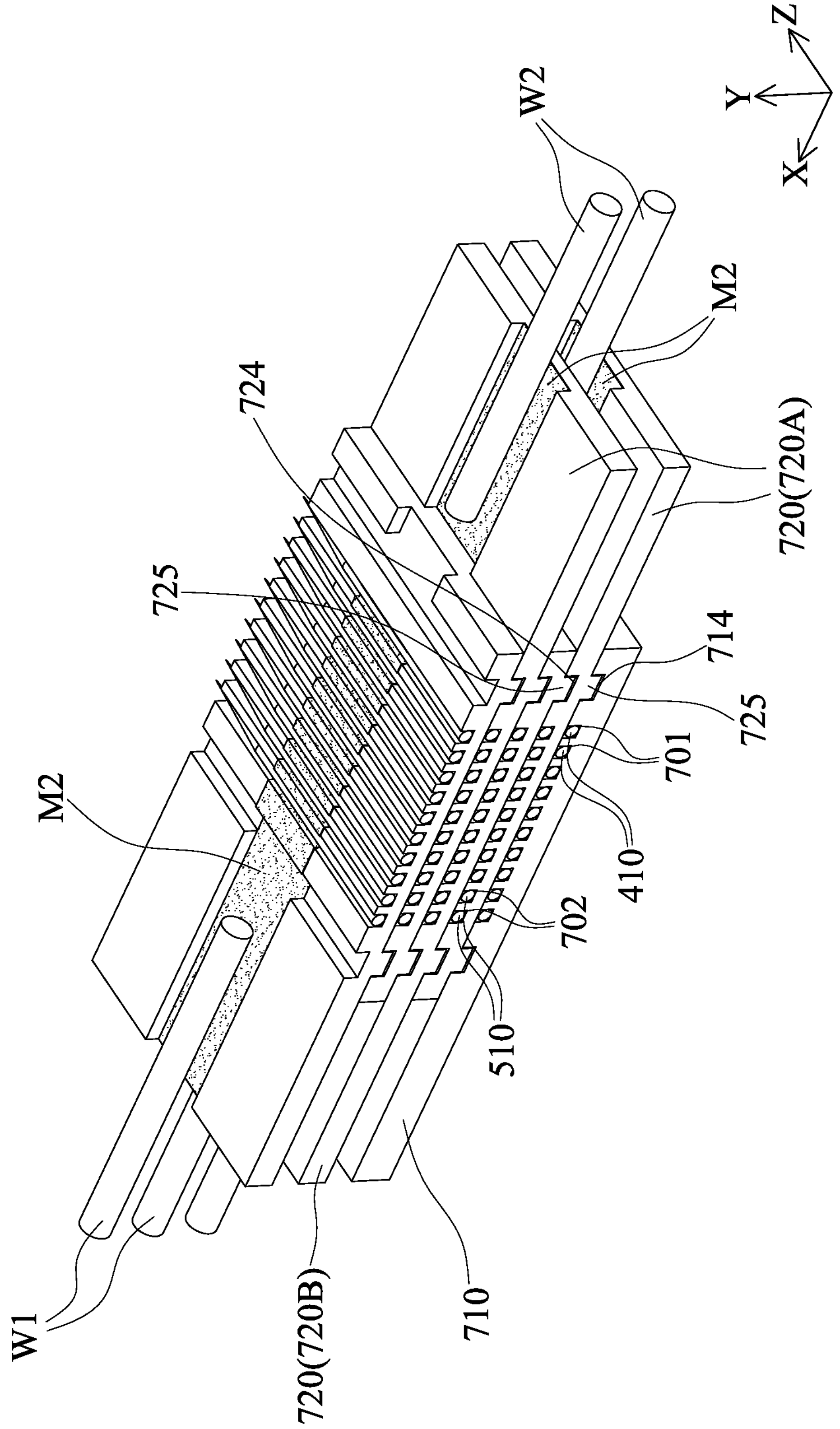
FIG. 11 is a schematic diagram of the first plate, the second plates, the first wire, the second wire, the first microneedle assemblies, and the second microneedle assemblies according to another embodiment of the invention.
Figure 12:
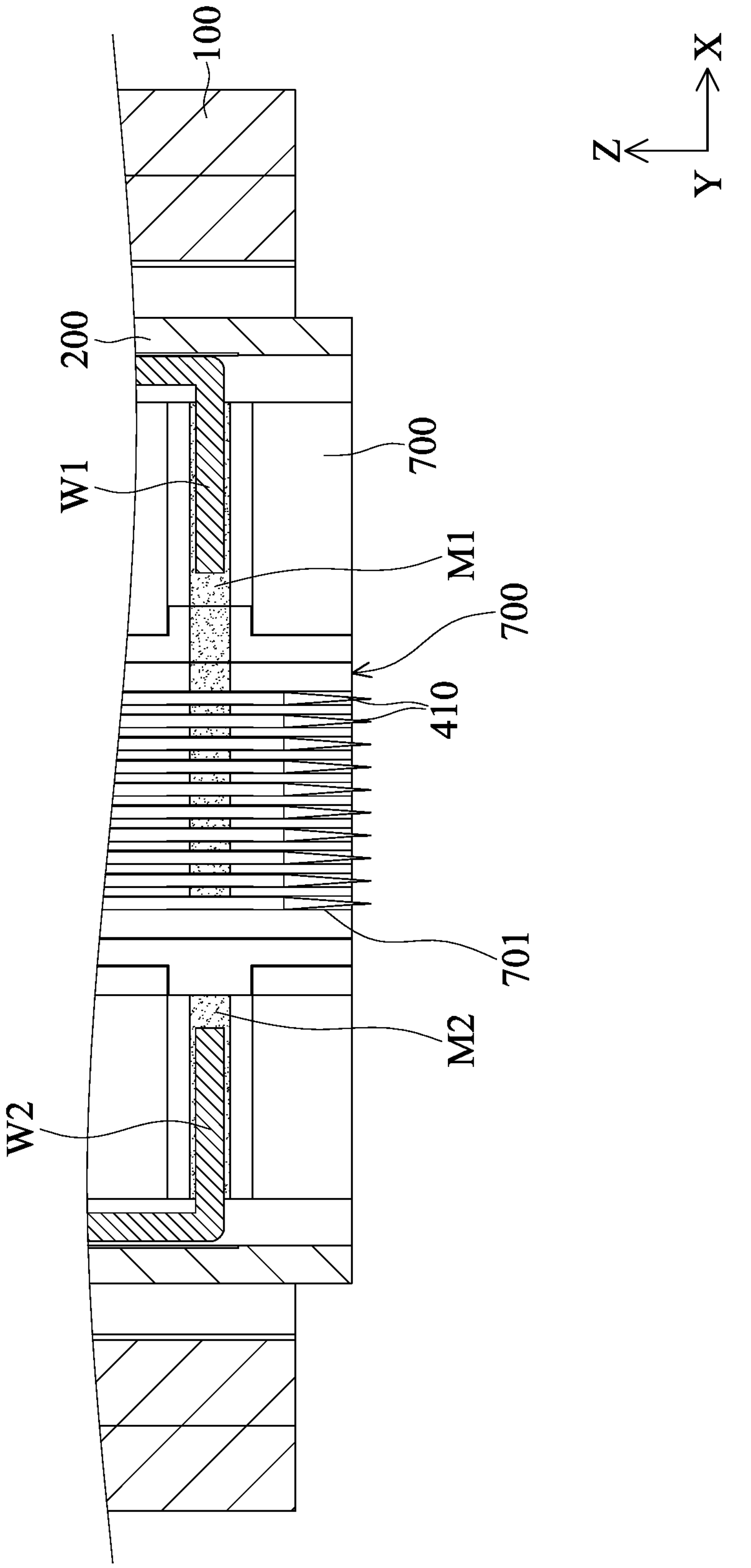
FIG. 12 is a partial cross-sectional view of the microneedle electroporation device according to another embodiment of the invention.

Referring to FIG. 9, FIG. 11, and FIG. 12, each of the first microneedle assemblies 400 includes a plurality of first microneedles 410. These first microneedles 410 pass through the first holes 701 of the intermediate module 700 and protrude from the intermediate module 700. Since the first metal plating film M1 is attached on the inner surface of each of the first holes 701, the first microneedles 410 can be in contact with the first metal plating film M1, and the first microneedles 410 can be electrically connected to the first metal plating film M1. Furthermore, the first metal plating film M1 is also in contact with the first wire W1.

Figure 13:
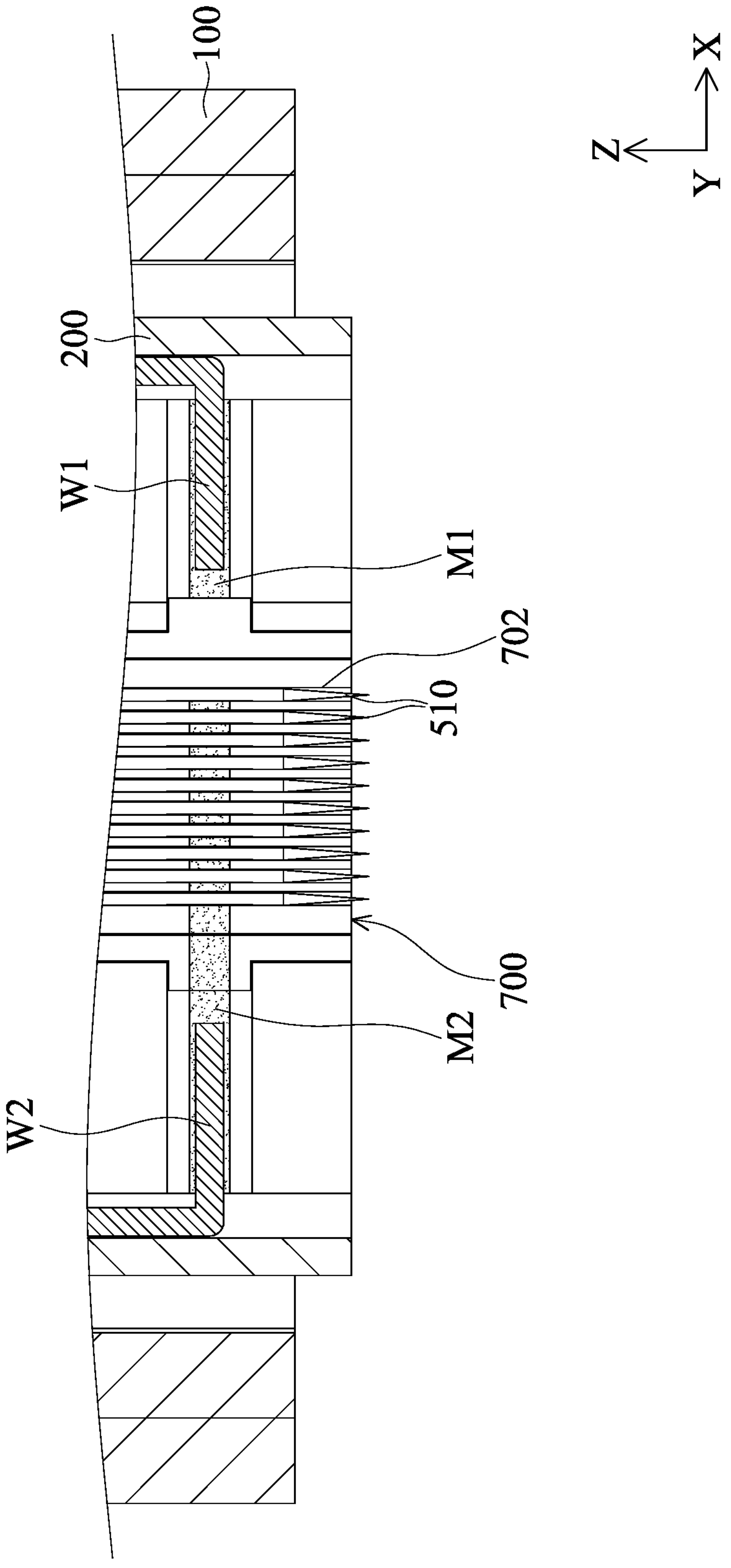
FIG. 13 is a partial cross-sectional view of the microneedle electroporation device according to another embodiment of the invention.

Referring to FIG. 9, FIG. 11, and FIG. 13, each of the second microneedle assemblies 500 includes a plurality of second microneedles 510. These second microneedles 510 pass through the second holes 702 of the intermediate module 700 and protrude from the intermediate module 700. Since the second metal plating film M2 is attached on the inner surface of each of the second holes 702, the second microneedles 510 can be in contact with the second metal plating film M2, and the second microneedles 510 can be electrically connected to the second metal plating film M2. Furthermore, the second metal plating film M2 is also in contact with the second wire W2. The first microneedle assemblies 400 and the second microneedle assemblies 500 can include suitable conductive material (such as other metal material) or a structure with a conductive layer covered on an insulating material.

Figure 14:
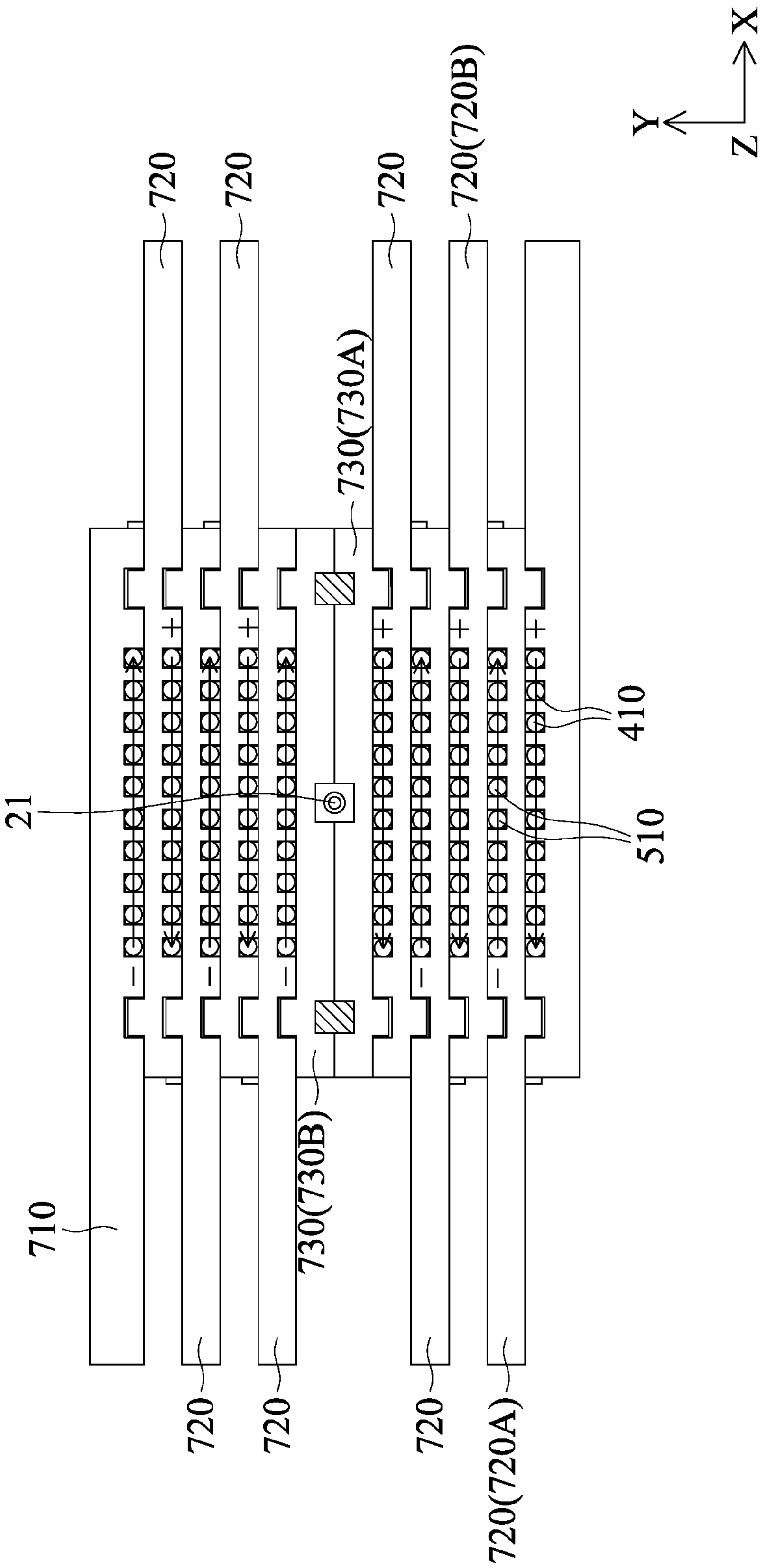
FIG. 14 is a schematic diagram that represents that an external power feeding device produces poles on the microneedle electroporation device according to another embodiment of the invention.

Referring to FIG. 8, in this embodiment, the socket 600 is disposed on the housing 100, and can be electrically connected to the external power feeding device. In particular, the socket 600 includes two inserting holes 610 and 620. The inserting hole 610 is electrically connected to the first microneedle assemblies 400 via the first wire W1, and the inserting hole 620 is electrically connected to the second microneedle assemblies 500 via the first wire W2. The external power feeding device can apply a bias voltage through the inserting holes 610 and 620, and produce an electric field between the first microneedles 410 and the second microneedles 510. For example, as shown in FIG. 11 and FIG. 14, the external power feeding device can form a positive pole on the first microneedles 410 of the first microneedle assemblies 400 via the first wire W1, and form a negative pole on the second microneedles 510 of the second microneedle assemblies 500 via the second wire W2.

Figure 15:
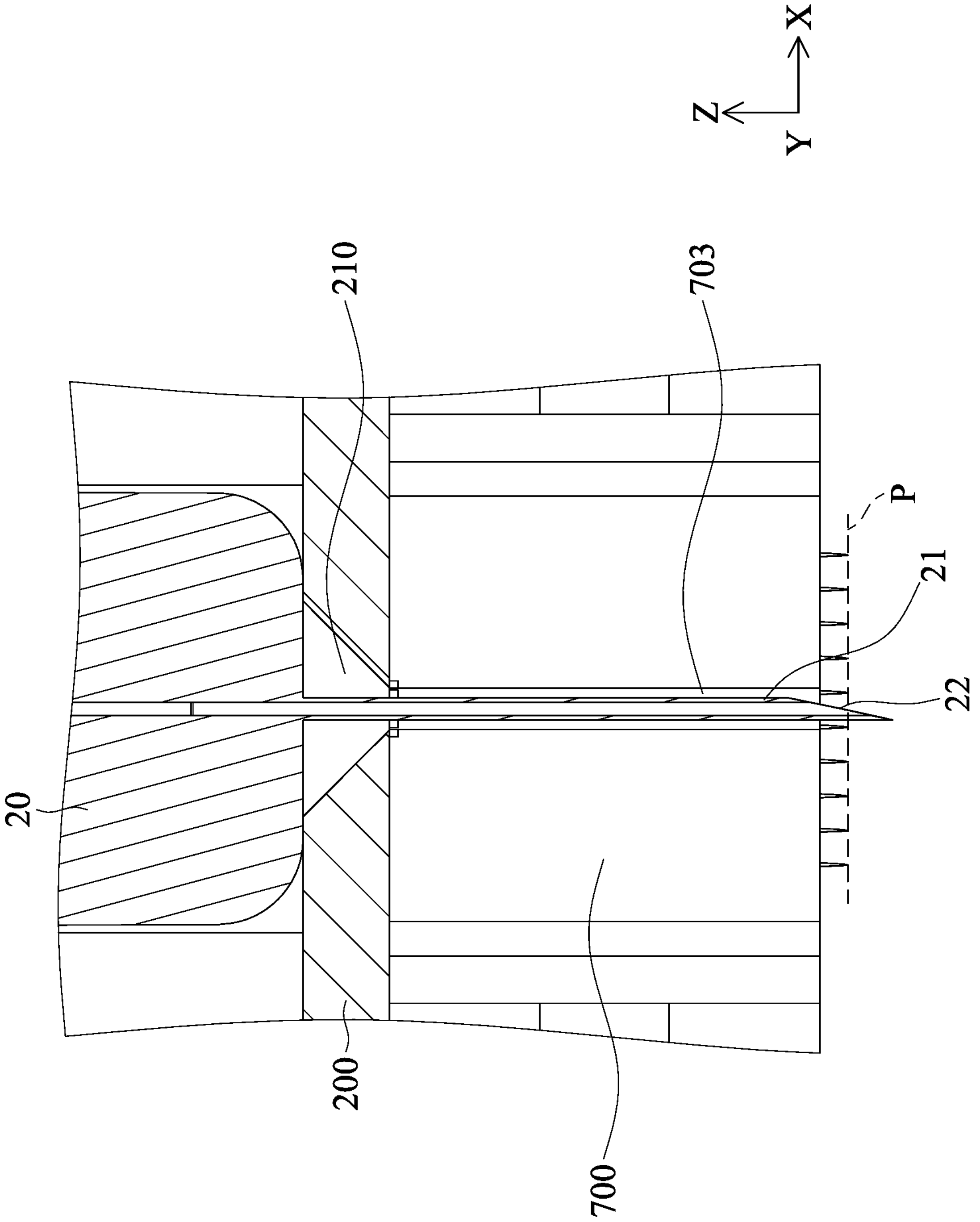
FIG. 15 is a schematic diagram of the microneedle electroporation device connected to the injecting device according to another embodiment of the invention.

As shown in FIG. 15, when the injecting device 20 enters the accommodating space 110 of the housing 100 and connects to the microneedle electroporation device 10', the needle head 21 of the injecting device 20 passes through the through hole 703 of the intermediate module 700, and the injecting device 20 is in contact with the positioning member 200 and/or the housing 100 to position the opening 22 of the needle head 21 relative to the intermediate module 700.

In this embodiment, the length of each of the first microneedles 410 is substantially the same as the length of each of the first microneedles 510 in the Z-axis, so that theirs ends are substantially disposed on a virtual plane P. After positioning, the opening 22 of the needle head 21 of the injecting device 20 overlaps the virtual plane P. Thus, it can be ensured that when the injecting device 20 injects the liquid, the microneedle electroporation device 10' can form the electric field around the injecting position of the injecting liquid in a similar depth by the first microneedles 410 and the second microneedles 510.

Figure 16:
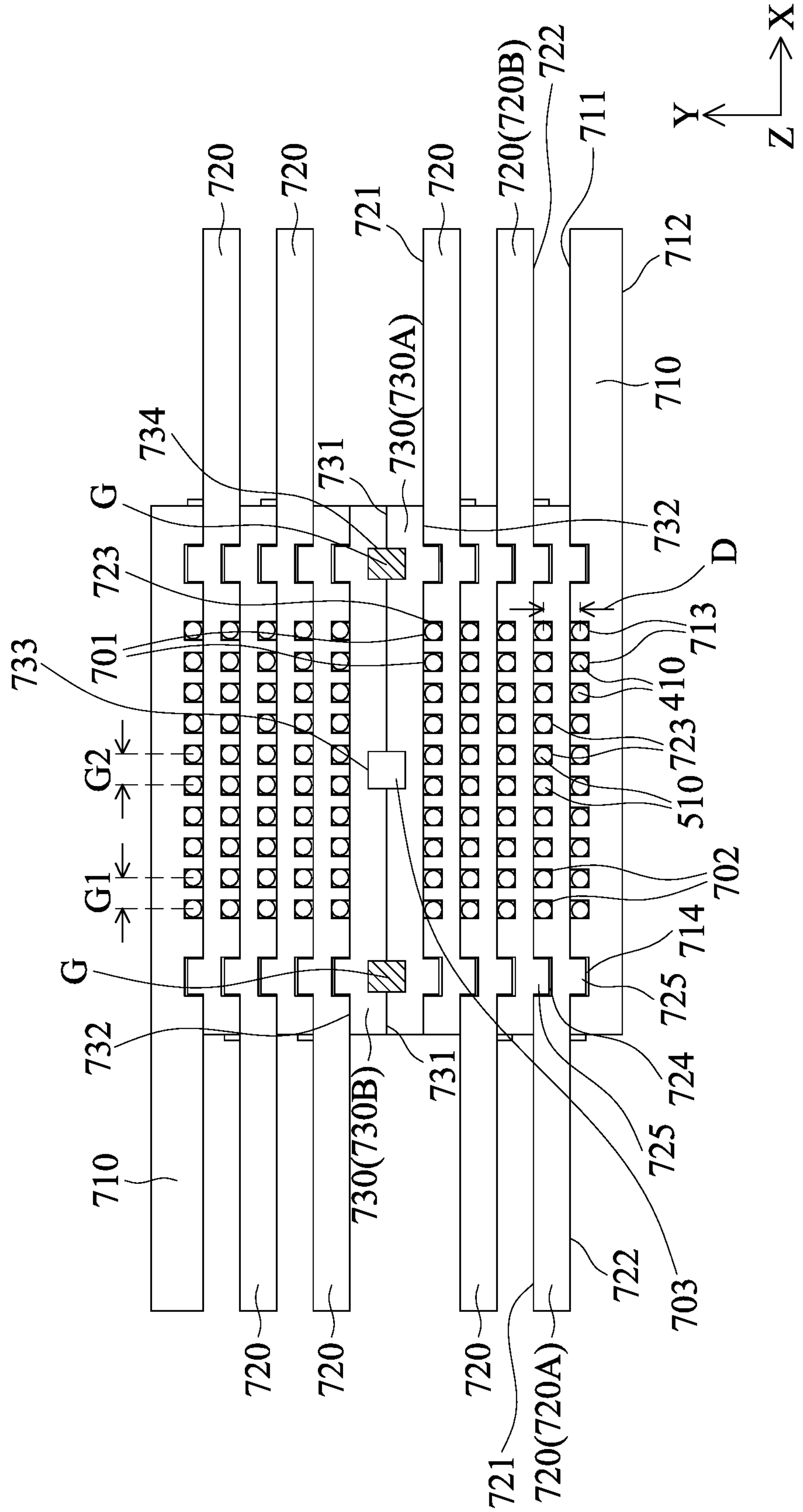
FIG. 16 is a schematic diagram of the first microneedle assemblies, the second microneedle assemblies, and the intermediate module according to another embodiment of the invention.

In this embodiment, the first microneedles 410 and the second microneedles 510 protrude from the intermediate module 700 about 0.03 mm-3.00 mm. Therefore, when they insert into the skin of the human, they can be substantially disposed at the epidermis to the dermis. Since there are more immune cells in this area, when the aforementioned microneedle structure applies the electric field to the cells to open the cell membranes and let the vaccine entering the cells, the immune response of the human can be increased, and the dosage of the vaccine can be reduced. As shown in FIG. 16, the gap G1 between the first microneedles 410 and the gap G2 between the second microneedles 510 respectively correspond to the gap between the first grooves 713 in the same plate and the gap between the second grooves 723 in the same plate. In an embodiment, the aforementioned gaps are arranged in 50 um-1000 um. The microneedles can be easily inputted into the holes by the corresponding gaps. The distance D between the first microneedles 410 and the second microneedles 510 is determined by the distance between the first grooves 713 and the second grooves 723. The aforementioned distance can be adjusted according to the required electric field, the voltage desired to apply (for example, less than 100V), and the position where the electroporation is applied on. In the smaller distance, the voltage required to achieve the same electric field can be effectively reduced. In an embodiment, the distance is ranged in 50 um-1000 um. The number of microneedle arrays formed by the first microneedles 410 and the second microneedles 510 can be determined by the number of the grooves on the plate and the number of stacked plates. As shown in FIG. 10A, the first and second plates of the intermediate module 700 include ten first grooves 713 and ten second grooves 723, and the intermediate module 700 is formed by stacking two first plates, eight second plates, and two third plates. 10×10 hole arrays can be therefore formed. When all of the microneedles are disposed in the holes, 10×10 microneedle arrays are formed. Similarly, the microneedles can be disposed in part of the holes to form the different microneedle arrays. Thus, the number of the microneedles in the microneedle arrays can be easily changed by the different numbers of the grooves on the plate, the numbers of the layers of the stacked plates, and the numbers of the microneedles disposed in the grooves.

In some embodiments (not shown), the first metal plating film M1 and the second metal plating film M2 can be omitted, and the first microneedle assemblies 400 and the second microneedle assemblies 500 can be replaced by the types shown in FIGS. 5A and 6A. The first wire W1 can connect the inserting hole 610 to the first metal connecting portion 420 to electrically connect the inserting hole 610 to the first microneedles 410, and the second wire W2 can connect the inserting hole 620 to the second metal connecting portion 520 to electrically connect the inserting hole 620 to the second microneedles 510. After assembled, the positioning member 200, the intermediate module 700, the first microneedle assemblies 400, and the second microneedle assemblies 500 can form an integrated component having the microneedle arrays. Thus, the user can easily replace it after used. In some embodiments, the housing 100 and the positioning member 200 can be integrally formed in one piece. Moreover, the electroporation device in this embodiment can be easily engaged with the syringe in the market, so as to have the functions of injection and electroporation together.

In summary, a microneedle electroporation device is provided, including a housing, a positioning member, an intermediate plate, a first microneedle assembly, a second microneedle assembly, a socket, a first wire, and a second wire. The housing has an accommodating space, and the positioning member is connected to the housing. The intermediate plate is connected to the positioning member, and includes a first surface, a second surface, a plurality of first holes, and a plurality of second holes, wherein the first surface faces the accommodating space, and the second surface is opposite to the first surface. The first holes and the second holes penetrate the intermediate plate from the first surface to the second surface. The first microneedle assembly is disposed between the positioning member and the intermediate plate, and includes a plurality of first microneedles and a first metal connecting portion. The first microneedles pass through the first holes, and the first metal connecting portion is connected to the first microneedles. The second microneedle assembly is disposed between the positioning member and the intermediate plate, and includes a plurality of second microneedles and a second metal connecting portion. The second microneedles pass through the second holes, and the second metal connecting portion is connected to the second microneedles. The first microneedle assembly and the second microneedle assembly are electrically independent of each other. The socket is disposed on the housing. The first wire connects the socket to the first metal connecting portion. The second wire connects the socket to the second metal connecting portion.

A microneedle electroporation device is also provided, including a housing, a positioning member, an intermediate module, a first microneedle assembly, a second microneedle assembly, a socket, a first wire, and a second wire. The housing has an accommodating space, and the positioning member is connected to the housing. The intermediate module is connected to the positioning member, and includes a plurality of plates, wherein a plurality of first holes and a plurality of second holes are formed between the plates. The first microneedle assembly includes a plurality of first microneedles. The first microneedles pass through the first holes, and are electrically connected to each other. The second microneedle assembly includes a plurality of second microneedles. The second microneedles pass through the second holes, and are electrically connected to each other. The socket is disposed on the housing. The first microneedle is electrically connected to the socket via the first wire. The second microneedle is electrically connected to the socket via the second wire.

Although some embodiments of the present disclosure and their advantages have been described in detail, it should be understood that various changes, substitutions and alterations can be made herein without departing from the spirit and scope of the disclosure as defined by the appended claims. For example, it will be readily understood by those skilled in the art that many of the features, functions, processes, and materials described herein may be varied while remaining within the scope of the present disclosure. Moreover, the scope of the present application is not intended to be limited to the particular embodiments of the process, machine, manufacture, compositions of matter, means, methods and steps described in the specification. As one of ordinary skill in the art will readily appreciate from the disclosure of the present disclosure, processes, machines, manufacture, compositions of matter, means, methods, or steps, presently existing or later to be developed, that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps. Moreover, the scope of the appended claims should be accorded the broadest interpretation so as to encompass all such modifications and similar arrangements.

While the invention has been described by way of example and in terms of preferred embodiment, it should be understood that the invention is not limited thereto. On the contrary, it is intended to cover various modifications and similar arrangements (as would be apparent to those skilled in the art). Therefore, the scope of the appended claims should be accorded the broadest interpretation to encompass all such modifications and similar arrangements.

What is claimed is:

1. A microneedle electroporation device, configured to be connected to an injecting device, wherein the microneedle electroporation device comprises:

- a housing, having an accommodating space;
- a positioning member, connected to the housing;
- an intermediate plate, connected to the positioning member, and comprising:
  - a first surface, facing the accommodating space;
  - a second surface, opposite to the first surface;
  - a plurality of first holes, penetrating the intermediate plate from the first surface to the second surface; and
  - a plurality of second holes, penetrating the intermediate plate from the first surface to the second surface;
- a first microneedle assembly, disposed between the positioning member and the intermediate plate, and comprising:
  - a plurality of first microneedles, passing through the first holes; and
  - a first metal connecting portion, connected to the first microneedles;
- a second microneedle assembly, disposed between the positioning member and the intermediate plate, and comprising:
  - a plurality of second microneedles, passing through the second holes; and
  - a second metal connecting portion, connected to the first microneedles, wherein the first microneedle assembly and the second microneedle assembly are electrically independent of each other;

a socket, disposed on the housing;

a first wire, electrically connected to the socket and the first metal connecting portion; and a second wire, electrically connected to the socket and the second metal connecting portion.

2. The microneedle electroporation device as claimed in claim 1, wherein the intermediate plate further comprises a first slot and a second slot, the first slot is in communication with the first holes, the second slot is in communication with the second holes, the first metal connecting portion is accommodated in the first slot, and the second connecting portion is accommodated in the second slot.

3. The microneedle electroporation device as claimed in claim 2, wherein the intermediate plate further comprises a first depression portion and a second depression portion that are formed on the first surface, and the first holes and the second holes are disposed between the first depression portion and the second depression portion, wherein the first slot is in communication with the first depression portion and separated from the second depression portion, and the second slot is in communication with the second depression portion and separated from the first depression portion.

4. The microneedle electroporation device as claimed in claim 1, wherein the microneedle electroporation device comprises a plurality of first microneedle assemblies and a plurality of second microneedle assemblies, and the first microneedle assemblies and the second microneedle assemblies are arranged on the intermediate plate in a staggered arrangement.

5. The microneedle electroporation device as claimed in claim 1, wherein the intermediate plate further comprises a through hole penetrating the intermediate plate from the first surface to the second surface, and the dimensions of the through hole are larger than the dimensions of each of the first holes and the dimensions of each of the second holes.

6. The microneedle electroporation device as claimed in claim 5, wherein the ends of the first microneedles and the second microneedles are disposed on a virtual plane, and when the injecting device is accommodated in the accommodating space and in contact with the positioning member, a needle head of the injecting device passes through the through hole, and an opening of the needle head overlaps the virtual plane.

7. The microneedle electroporation device as claimed in claim 1, wherein the first microneedles and the second microneedles protrude from the second surface 0.03 mm-3.00 mm.

8. The microneedle electroporation device as claimed in claim 1, wherein the first metal connecting portion is parallel to the second metal connecting portion.

9. A microneedle electroporation device, configured to be connected to an injecting device, wherein the microneedle electroporation device comprises:

a housing, having an accommodating space;

a positioning member, connected to the housing;

an intermediate module, connected to the positioning member, and comprising a plurality of plates, wherein a plurality of first holes and a plurality of second holes are formed between the plates;

a first microneedle assembly, comprising a plurality of first microneedles, wherein the first microneedles pass through the first holes and are electrically connected to each other;

a second microneedle assembly, comprising a plurality of second microneedles, wherein the second microneedles pass through the second holes and are electrically connected to each other;

a socket, disposed on the housing;

a first wire, wherein the first microneedles are electrically connected to the socket via the first wire; and a second wire, wherein the second microneedles are electrically connected to the socket via the second wire.

10. The microneedle electroporation device as claimed in claim 9, wherein the plates comprise:

at least one first plate, having a first top surface and a first bottom surface, wherein a plurality of first grooves are formed on the first top surface;

at least one second plate, having a second top surface and a second bottom surface, wherein the second bottom surface faces the first top surface, and a plurality of second grooves are formed on the second top surface; and at least one third plate, having a third top surface and a third bottom surface, wherein the third bottom surface faces the second top surface, the second plate is disposed between the first plate and the third plate, at least some of the first holes are formed by the first grooves, and at least some of the second holes are formed by the second grooves.

11. The microneedle electroporation device as claimed in claim 10, wherein the microneedle electroporation device further comprises a first metal plating film disposed on the first top surface, and the first metal plating film is in contact with the first microneedles and the first wire.

12. The microneedle electroporation device as claimed in claim 10, wherein the microneedle electroporation device further comprises a second metal plating film disposed on the second top surface, and the second metal plating film is in contact with the second microneedles and the second wire.

13. The microneedle electroporation device as claimed in claim 10, wherein the plates further comprise an additional second plate disposed between the second plate and the third plate, and the additional second plate comprises an additional second top surface and an additional second bottom surface, wherein the additional second bottom surface faces the second top surface, a plurality of additional second grooves are formed on the additional second top surface, and at least some of the first holes are formed by the additional second grooves.

14. The microneedle electroporation device as claimed in claim 13, wherein the microneedle electroporation device further comprises an additional second metal plating film disposed on the additional second top surface, and the additional second metal plating film is in contact with the first microneedles and the first wire.

15. The microneedle electroporation device as claimed in claim 10, wherein the first plate further comprises a positioning groove formed on the first top surface of the first plate, the second plate further comprises a positioning protrusion formed on the second bottom surface of the second plate, and the positioning protrusion is inserted into the positioning groove to fix the first and second plates in position.

16. The microneedle electroporation device as claimed in claim 10, wherein the microneedle electroporation device further comprises an additional third plate having an additional third top surface, and the additional third top surface is in contact with the third top surface, wherein a third groove and an additional third groove are respectively formed on the third top surface and the additional third top surface, and the third groove and the additional third groove are aligned with each other to form a through hole.

17. The microneedle electroporation device as claimed in claim 16, wherein the dimensions of the through hole are larger than the dimensions of each of the first holes and the dimensions of each of the second holes.

18. The microneedle electroporation device as claimed in claim 16, wherein the ends of the first microneedles and the second microneedles are disposed on a virtual plane, and when the injecting device is accommodated in the accommodating space and in contact with the positioning member, the needle head of the injecting device passes through the through hole, and an opening of the needle head overlaps the virtual plane.

19. The microneedle electroporation device as claimed in claim 9, wherein the first microneedle assembly further comprises a first metal connecting portion electrically connected to the first microneedles and the first wire, and the second microneedle assembly further comprises a second metal connecting portion electrically connected to the second microneedles and the second wire.

20. The microneedle electroporation device as claimed in claim 9, wherein the first microneedles protrude from the intermediate module 0.03 mm-3.00 mm.

* * * * *